(12) United States Patent
Urano et al.

(10) Patent No.: US 11,591,359 B2
(45) Date of Patent: Feb. 28, 2023

(54) ENZYME-SPECIFIC INTRACELLULARLY-RETAINED RED FLUORESCENT PROBE

(71) Applicant: The University of Tokyo, Tokyo (JP)

(72) Inventors: Yasuteru Urano, Tokyo (JP); Mako Kamiya, Tokyo (JP); Hiroki Ito, Tokyo (JP); Yu Kawamata, Tokyo (JP)

(73) Assignee: The University of Tokyo, Tokyo (JP)

( * ) Notice: Subject to any disclaimer, the term of this patent is extended or adjusted under 35 U.S.C. 154(b) by 1065 days.

(21) Appl. No.: 16/313,357

(22) PCT Filed: Jun. 23, 2017

(86) PCT No.: PCT/JP2017/023171
§ 371 (c)(1),
(2) Date: Apr. 25, 2019

(87) PCT Pub. No.: WO2018/003686
PCT Pub. Date: Jan. 4, 2018

(65) Prior Publication Data
US 2019/0256544 A1    Aug. 22, 2019

(30) Foreign Application Priority Data
Jun. 30, 2016 (JP) .............................. JP2016-130024

(51) Int. Cl.
*C07H 17/04* (2006.01)
*C12Q 1/34* (2006.01)
(Continued)

(52) U.S. Cl.
CPC .............. *C07H 17/04* (2013.01); *C07H 17/00* (2013.01); *C09K 11/06* (2013.01); *C12Q 1/28* (2013.01);
(Continued)

(58) Field of Classification Search
CPC ........ C07H 17/00; C07H 17/04; C09K 11/06; C12Q 1/28; C12Q 1/34; C12Q 1/42;
(Continued)

(56) References Cited

U.S. PATENT DOCUMENTS

| | | |
|---|---|---|
| 2008/0014602 A1 | 1/2008 | Nagano et al. |
| 2014/0342384 A1 | 11/2014 | Nagano et al. |
| 2015/0353585 A1 | 12/2015 | Nagano et al. |
| 2016/0356796 A1 | 12/2016 | Nagasawa et al. |
| 2017/0073321 A1 | 3/2017 | Urano et al. |

FOREIGN PATENT DOCUMENTS

| | | |
|---|---|---|
| WO | 2005024049 | 3/2005 |
| WO | 2014106957 | 7/2014 |
| WO | 2012111818 | 8/2014 |

(Continued)

OTHER PUBLICATIONS

Hirabayashi et al. Anal. Chem. (Aug. 3, 2015) 87: 9061-9069 (Year: 2015).*
Kenjiro Hanaoka et al., "Development of Silicon-substituted Xanthene Dyes and Their Application to Fluorescent Probes", Journal of Synthetic Organic Chemistry, Japan, May 1, 2016 (May 1, 2016), vol. 74, pp. 512-520.
Wang, Baogang et al., A general approach to spirolactonized Si-rhodamines, Chem. Commun., 2014, vol. 50, pp. 14374-14377.
Asanuma, Daisuke et al., Sensitive beta-galactosidase-targeting fluorescence probe for visualizing small peritoneal metastatic tumours in vivo, Nat. Commun., 2015, vol. 6: 6463, pp. 1-7.
Egawa, Takahiro et al., Development of a fluorescein analogue, TokyoMagenta, as a novel scaffold for fluorescence probes in red region,Chem. Commun., 2011, vol. 47, pp. 4162-4164.
(Continued)

*Primary Examiner* — Susan M Hanley
(74) *Attorney, Agent, or Firm* — Leason Ellis LLP

(57) ABSTRACT

It is an object of the present invention to provide a fluorescence imaging probe capable of selectively visualizing target cells such as cells expressing β-galactosidase (lacZ expressing cells) at a single-cell level in a red fluorescence region, and of performing co-staining together with GFP.
An intracellularly-retainable red fluorescent probe comprising a compound represented by the following formula (I) or a salt thereof:

[Chemical Formula 1]

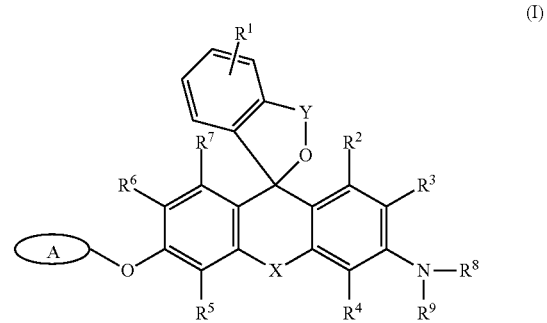

wherein: A represents a monovalent group cleaved by an enzyme; $R^1$ represents
a hydrogen atom, or one to four of the same or different substituents bonded to a benzene ring; $R^3$, $R^4$, $R^5$, and $R^6$ each independently represent $-CFR^{10}R^{11}$, $-CF_2R^{12}$, a hydrogen atom, a hydroxyl group, an alkyl group, or a halogen atom, wherein at least one of $R^3$, $R^4$, $R^5$, and $R^6$ is $-CFR^{10}R^{11}$ or $-CF_2R^{12}$;
$R^2$ and $R^7$ each independently represent a hydrogen atom, a hydroxyl group, an alkyl group, or a halogen atom; $R^8$ and $R^9$ each independently represent a hydrogen atom or an alkyl group; $R^{10}$, $R^{11}$, and $R^{12}$ each independently represent a hydrogen atom, an alkyl group, or an alkenyl group; X represents Si($R^a$) ($R^b$), wherein $R^a$ and $R^b$ each independently represent a hydrogen atom or an alkyl group; and Y is $-C(=O)-$ or $-R^cC(=O)-$, wherein $R^c$ is an alkylene group having 1-3 carbon atoms.

15 Claims, 4 Drawing Sheets

(51) Int. Cl.
- *G01N 33/58* (2006.01)
- *C09K 11/06* (2006.01)
- *G01N 33/52* (2006.01)
- *G01N 33/574* (2006.01)
- *C12Q 1/28* (2006.01)
- *C07H 17/00* (2006.01)
- *C12Q 1/54* (2006.01)
- *C12Q 1/66* (2006.01)
- *C12Q 1/42* (2006.01)

(52) U.S. Cl.
CPC ............... *C12Q 1/34* (2013.01); *C12Q 1/42* (2013.01); *C12Q 1/54* (2013.01); *C12Q 1/66* (2013.01); *G01N 33/52* (2013.01); *G01N 33/574* (2013.01); *G01N 33/58* (2013.01); *G01N 33/582* (2013.01); *C12Q 2563/107* (2013.01)

(58) Field of Classification Search
CPC ...... C12Q 1/54; C12Q 1/66; C12Q 2563/107; G01N 33/52; G01N 33/574; G01N 33/58; G01N 33/582
See application file for complete search history.

(56) References Cited

FOREIGN PATENT DOCUMENTS

| WO | 2015108172 | 7/2015 |
|---|---|---|
| WO | 2015174460 | 11/2015 |

OTHER PUBLICATIONS

International Search Report and Written Opinion dated Sep. 19, 2017 corresponding to International Patent Application No. PCT/JP2017/023171; 16 pages.

Dimri et al., A biomarker that identifies senescent human cells in culture and in aging skin in vivo, Proc. Natl. Acad. Sci. USA, 1995, 92, pp. 9363-9367.

Bosmann et al., Enzyme Activity in Invasive Tumors of Human Breast and Colon, Proc. Natl. Acad. Sci. USA, 1974, 71:5, pp. 1833-1837.

Chatterjee et al., Glycosyltransferase and Glycosidase Activities in Ovarian Cancer Patients, Cancer Res., 1979, 39, pp. 1943-1951.

Debacq-Chainiaux et al., Protocols to detect senescence-associated beta-galactosidase (SA-βgal) activity, a biomarker of senescent cells in culture and in vivo, Nat. Protoc., 2009, 4:12, pp. 1798-1806.

Kamiya et al., β-Galactosidase Fluorescence Probe with Improved Cellular Accumulation Based on a Spirocyclized Rhodol Scaffold, J. Am. Chem. Soc. 2011, 133, pp. 12960-12963.

* cited by examiner

[Fig. 1]
(a)
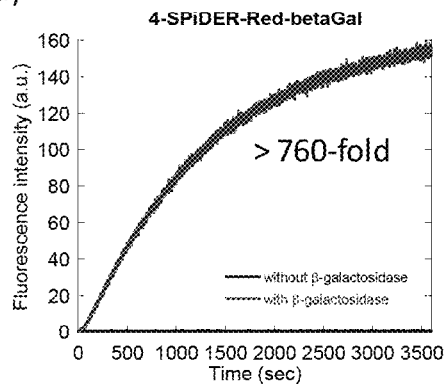
(b)
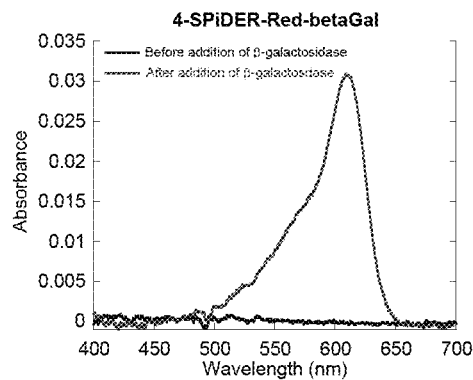
(c)
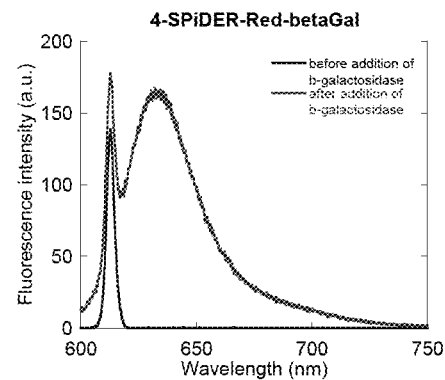

[Fig. 2]
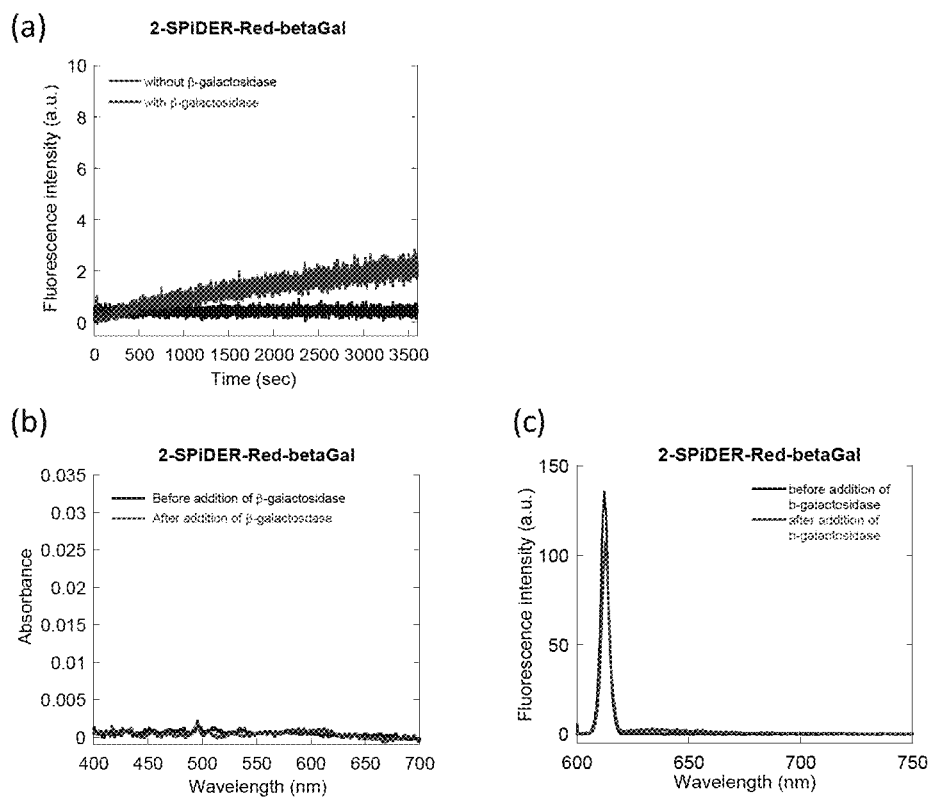
[Fig. 3]
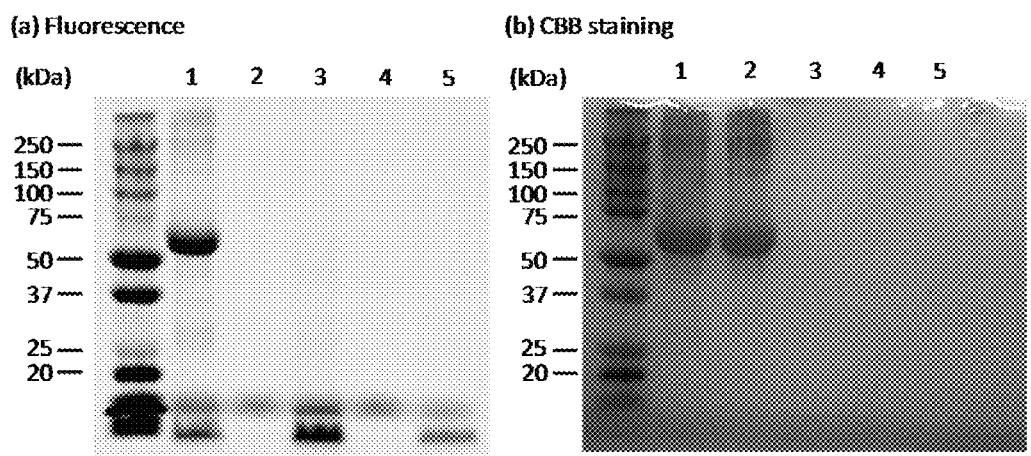

[Fig. 4]
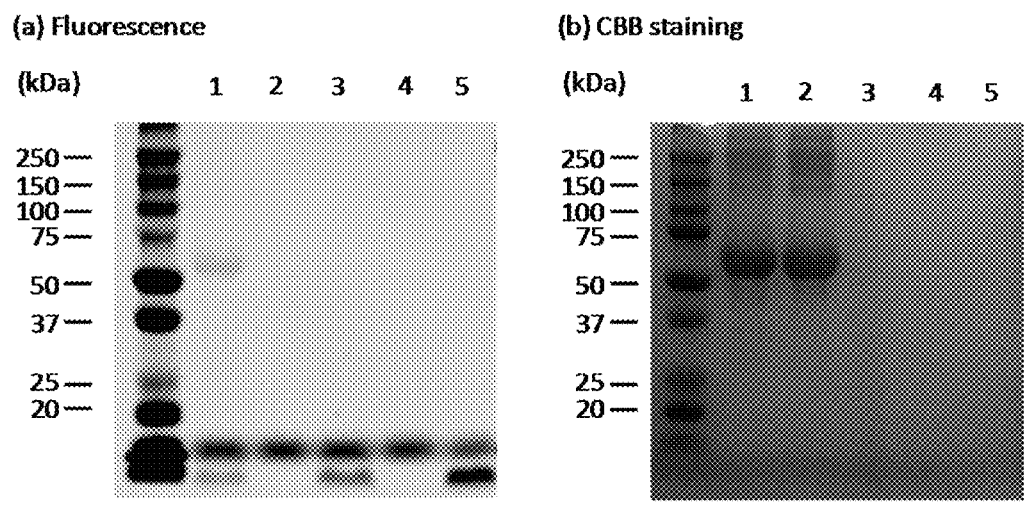
[Fig. 5]
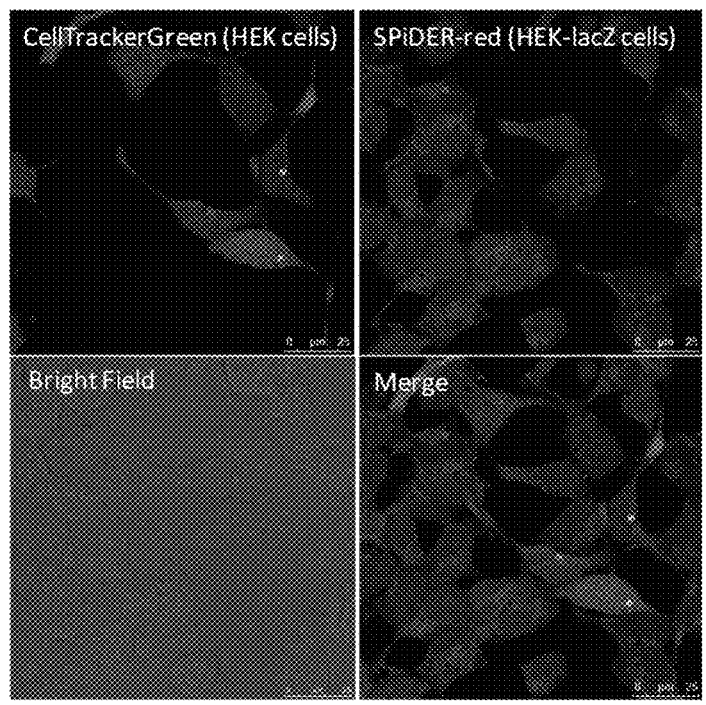

[Fig. 6]
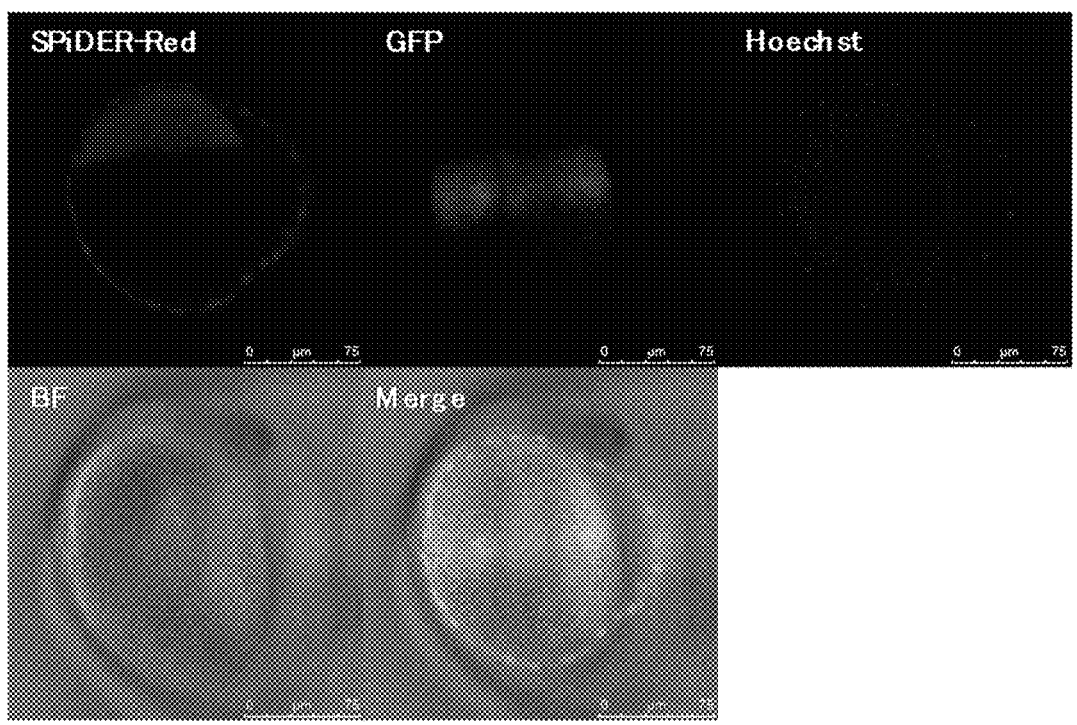

ENZYME-SPECIFIC INTRACELLULARLY-RETAINED RED FLUORESCENT PROBE

TECHNICAL FIELD

The present invention relates to a novel red fluorescent probe which can be retained in a target cell and can act specifically in the cell, a method for specifically imaging a target cell expressing a specific enzyme using the fluorescent probe, and a detection kit including the probe.

BACKGROUND ART

Reporter proteins have made an immeasurable contribution to the development of life sciences. The most commonly used reporter protein is β-galactosidase (lacZ). A relationship between aging and expression of β-galactosidase in cells has recently been suggested (see Non-Patent Literature 1), and imaging probes which are enzyme-specific to β-galactosidase are important molecular tools for elucidating mechanisms of cell aging. Furthermore, β-galactosidase activity has been shown to be elevated in certain types of cancer cells (see Non-Patent Literatures 2 and 3), and an imaging probe which is enzyme-specific to β-galactosidase is thought to be usable also as a cancer-cell-selective fluorescence imaging probe.

Conventionally, techniques for imaging enzyme activity using X-Gal as a substrate are widely used (Non-Patent Literature 4), but X-Gal cannot be applied to living cells, and therefore, a probe for imaging enzyme activity which can be applied to living cells is desired to be developed. Numerous imaging probes that can be applied to living cells have presently been developed. For example, HMDER-βGal and the like have been developed as β-galactosidase fluorescent probes which can be applied to living cells and living biological tissues, and in which visible light excitation is possible by control of a spiro-ring-forming reaction in the molecule thereof (see Non-Patent Literature 5 and Patent Literature 1).

However, from problem points such as low cell membrane permeability and low intracellular retention of a fluorescent dye generated after an enzyme reaction, in the conventional β-galactosidase fluorescent probes, living cells and the like are difficult to clearly image at a single-cell level. On the other hand, the present inventors developed an imaging probe in which a fluoromethyl group is introduced into a xanthene ring (Patent Literature 2). The probe can detect a target cell at a single-cell level, but luminescence in fluorescence detection is in a green fluorescence region, which makes it difficult to perform co-staining together with GFP (green fluorescent protein) which is frequently used in live imaging.

CITATION LIST

Patent Literature

Patent Literature 1: International Publication 2005/024049
Patent Literature 2: International Publication 2015/174460

Non Patent Literature

Non Patent Literature 1: G. P. Dimri et al., Proc. Natl. Acad. Sci. USA, 1995, 92, pp. 9363-9367.
Non Patent Literature 2: H. B. Bosmann et al., Proc. Natl. Acad. Sci. USA, 1974, 71, pp. 1833-1837.
Non Patent Literature 3: S. K. Chatterjee et al. Cancer Res., 1979, 39, pp. 1943-1951.
Non Patent Literature 4: F. D.-Chainiaux et al., Nat. Protoc., 2009, 4, pp. 1798-1806.
Non-Patent Literature 5: M. Kamiya et al., J. Am. Chem. Soc. 2011, 133, pp. 12960-12963.

SUMMARY OF INVENTION

Technical Problem

Therefore, it is an object of the present invention to provide a fluorescence imaging probe capable of selectively visualizing target cells such as cells expressing β-galactosidase (lacZ expressing cells) at a single-cell level in a red fluorescence region, and of performing co-staining together with GFP.

Solution to Problem

As a result of intensive studies to solve the above problems, the present inventors have found that, by substituting an oxygen atom as a 10-position element of a xanthene ring in a rhodamine-based fluorescent dye with a silicon atom, using a derivative having a substituent based on carboxyl group at a 2-position of a benzene ring, and introducing a substituent which changes the derivative into a quinone methide by a reaction with an enzyme into the derivative, a fluorescence imaging probe is obtained, which has excellent intracellular retention, and in which red fluorescence is exhibited only by a reaction with an enzyme such as β-galactosidase. By combining the fact that the quinone methide having high reactivity is produced by the reaction between the fluorescent probe and the enzyme, and is covalently bonded to an intracellular nucleophilic molecule such as protein irreversibly, with control of fluorescence due to intramolecular spirocyclization equilibrium in the fluorescent probe, the above-mentioned problem is solved to allow the live image of target cells. The inventors completed the present invention based on these findings.

That is, in one aspect, the present invention provides
<1> An intracellularly-retainable red fluorescent probe including a compound represented by the following formula (I) or a salt thereof:

[Chemical Formula 1]

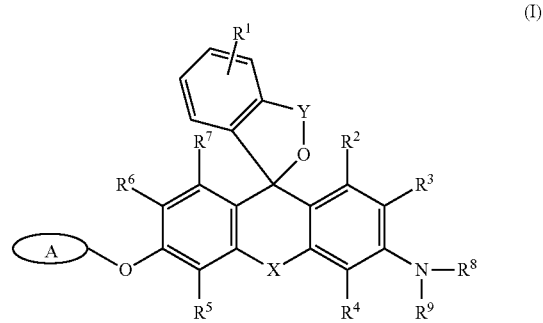

wherein:
A represents a monovalent group cleaved by an enzyme;
$R^1$ represents a hydrogen atom, or one to four of the same or different substituents bonded to a benzene ring; $R^3$, $R^4$, $R^5$, and R$^6$ each independently represent —CFR$^{10}$R$^{11}$, —CF$_2$R$^{12}$, a hydrogen atom, a hydroxyl group, an alkyl group, or a halogen atom, wherein at least one of R$^3$, R$^4$, R$^5$, and R$^6$ is —CFR$^{10}$R$^{11}$ or —CF$_2$R$^{12}$; R$^2$ and R$^7$ each independently represent a hydrogen atom, a hydroxyl group, an alkyl group, or a halogen atom; R$^8$ and R$^9$ each independently represent a hydrogen atom or an alkyl group; R$^{10}$, R$^{11}$ and R$^{12}$ each independently represent a hydrogen atom, an alkyl group, or an alkenyl group; X represents Si(R$^a$)(R$^b$), wherein R$^a$ and R$^b$ each independently represent a hydrogen atom or an alkyl group; and Y is —C(=O)— or —R$^c$C(=O)—, wherein R$^c$ is an alkylene group having 1-3 carbon atoms;

<2> The intracellularly-retainable red fluorescent probe according to the above <1>, wherein the enzyme is a hydrolase containing a reporter enzyme;

<3> The intracellularly-retainable red fluorescent probe according to the above <2>, wherein the reporter enzyme is β-galactosidase, β-lactamase, alkali phosphatase, luciferase, or peroxidase;

<4> The intracellularly-retainable red fluorescent probe according to the above <1>, wherein the enzyme is an enzyme expressed or activated specifically in a cancer cell;

<5> The intracellularly-retainable red fluorescent probe according to <1>, wherein A is a galactopyranosyl group;

<6> The intracellularly-retainable red fluorescent probe according to any one of the above <1> to <5>, wherein at least one of R$^3$, R$^4$, R$^5$, and R$^6$ is —CFR$^{10}$R$^{11}$;

<7> The intracellularly-retainable red fluorescent probe according to any one of the above <1> to <5>, wherein at least one of R$^3$, R$^4$, R$^5$, and R$^6$ is —CH$_2$F; and <8> An intracellularly-retainable red fluorescent probe including a compound represented by the following formula (Ia) or (Ib) or a salt thereof:

[Chemical Formula 2]

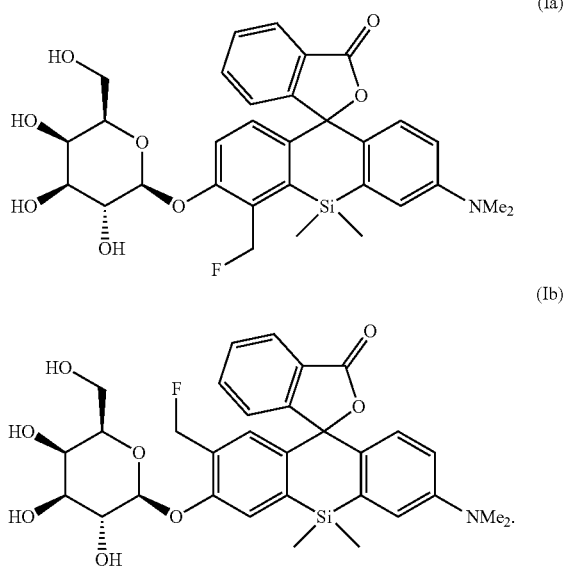

Also, in another aspect, the present invention provides

<9> A kit for detecting or visualizing a target cell expressing a specific enzyme,
the kit including the intracellularly-retainable red fluorescent probe according to any one of the above <1> to <8>;

<10> The composition or kit according to the above <9>, wherein the target cell is a cell expressing β-galactosidase;

<11> The composition or kit according to the above <9>, wherein the target cell is a cancer cell;

<12> A method for detecting a target cell expressing a specific enzyme by using the intracellularly-retainable red fluorescent probe according to any one of the above <1> to <8>;

<13> The method according to the above <12>, including the steps of: bringing the intracellularly-retainable red fluorescent probe into contact with an enzyme expressed specifically in the target cell at ex vivo; and inducing fluorescence by excitation light irradiation;

<14> The method according to the above <12> or <13>, wherein the target cell is a cell expressing β-galactosidase; and <15> The method according to the above <12> or <13>, wherein the target cell is a cancer cell.

Advantageous Effects of Invention

The intracellularly-retainable red fluorescent probe of the present invention exhibits advantageous effects that it has sufficient cell permeability and intracellular retention, can live-detect cells expressing a reporter enzyme such as β-galactosidase at a single-cell level, can be separated from a fluorescent signal of GFP (green fluorescent protein) because of a luminescent signal in a red fluorescence region, and can perform co-staining together with GFP. Therefore, according to the present invention, the use of a novel fluorescent probe having both red fluorescence and intracellular retention allows selective fluorescence imaging of target cells at a single-cell level in living cells and living biological tissues.

This makes it is possible to track changes in individual cells over time. For example, by selectively subjecting cancer cells to fluorescence imaging, cancer tissues can also be surgically excised without leaving the cancer tissues behind. Furthermore, an imaging technique using the intracellularly-retainable red fluorescent probe of the present invention can be implemented using a normal microscope capable of performing cell imaging and does not require a special device. Thus, the intracellularly-retainable red fluorescent probe of the present invention has extremely significant industrial utility value and economic effect.

BRIEF DESCRIPTION OF DRAWINGS

FIG. 1 is a graph showing the intensity (a), change in absorption spectrum (b), and fluorescence spectrum (c) of fluorescence generated by an enzyme reaction between 4-CH$_2$F-SPiDER-RED-βGal which is an intracellularly-retainable red fluorescent probe of the present invention and β-galactosidase.

FIG. 2 is a graph showing the intensity (a), change in absorption spectrum (b), and fluorescence spectrum (c) of fluorescence generated by an enzyme reaction between 2-CH$_2$F-SPiDER-RED-βGal which is an intracellularly-retainable red fluorescent probe of the present invention and β-galactosidase.

FIG. 3 is a view showing that protein BSA coexisting in a solution can be fluorescently labeled by an enzyme reaction between 4-CH$_2$F-SPiDER-RED-βGal which is an intracellularly-retainable red fluorescent probe of the present invention and β-galactosidase. (a) A fluorescence image obtained when an SDS-PAGE gel is excited by excitation light having a wavelength of 488 nm. Lane 1: 10 μL of a PBS buffer solution containing 10 μM 4-CH$_2$F-SPiDER-RED-βGal, 1 mg/mL BSA, and 5U β-galactosidase, Lane 2: 10 μL of a PBS buffer solution containing 10 μM 4-CH$_2$F-SPiDER-RED-βGal and 1 mg/mL BSA, Lane 3: 10 μL of a PBS buffer solution containing 10 μM 4-CH$_2$F-SPiDER-RED-βGal and 5U β-galactosidase, Lane 4: 10 μL of a PBS buffer solution containing only 10 μM 4-CH$_2$F-SPiDER-RED-βGal, Lane 5: 10 μL of a PBS buffer solution containing 10 μM 4-CH$_2$OH-SPiDER-RED. (b) Image of the abovementioned SDS-PAGE gel after Coomassie stained.

FIG. 4 is a view showing that protein BSA coexisting in a solution can be fluorescently labeled by an enzyme reaction between 2-CH$_2$F-SPiDER-RED-βGal which is an intracellularly-retainable red fluorescent probe of the present invention and β-galactosidase. (a) A fluorescence image obtained when an SDS-PAGE gel is excited by excitation light having a wavelength of 488 nm. Lane 1: 10 μL of a PBS buffer solution containing 10 μM 2-CH$_2$F-SPiDER-RED-βGal, 1 mg/mL BSA, and 5U β-galactosidase, Lane 2: 10 μL of a PBS buffer solution containing 10 μM 2-CH$_2$F-SPiDER-RED-βGal and 1 mg/mL BSA, Lane 3: 10 μL of a PBS buffer solution containing 10 μM 2-CH$_2$F-SPiDER-RED-βGal and 5U β-galactosidase, Lane 4: 10 μL of a PBS buffer solution containing only 10 μM 2-CH$_2$F-SPiDER-RED-βGal, Lane 5: 10 μL of a PBS buffer solution containing 10 μM 2-CH$_2$OH-SPiDER-RED. (b) Image of the abovementioned SDS-PAGE gel after Coomassie stained.

FIG. 5 shows a living cell fluorescence imaging image using 4-CH$_2$F-SPiDER-RED-βGal which is an intracellularly-retainable red fluorescent probe of the present invention. FIG. 5 shows images when cells expressing β-galactosidase (HEK-lacZ) and cells not expressing β-galactosidase (HEK, previously stained with CellTracker Green) were co-cultured and incubated with 4-CHF$_2$-SPiDER-RED-βGal. The upper left view shows an observation image of green fluorescence from an HEK cell; the upper right view shows an observation image of red fluorescence derived from 4-CH$_2$F-SPiDER-RED-βGal; the lower left view shows a bright field image; and the lower right view shows a superimposed image of fluorescent images. These views show that the intracellularly-retainable red fluorescent probe can be used for fluorescence imaging of living cells at a single-cell level.

FIG. 6 shows a fluorescence imaging image of wing primordia tissues reacted with 4-CHF$_2$-SPiDER-RED-βGal which is an intracellularly-retainable red fluorescent probe of the present invention. FIG. 6 includes a fluorescence image of 4-CHF$_2$-SPiDER-RED-βGal, a fluorescence image of GFP, and a fluorescence image of Hoechst 33342 in order from upper left, and a bright field image and a merged image thereof in order from lower left.

DESCRIPTION OF EMBODIMENTS

Hereinafter, embodiments of the present invention will be described. The scope of the present invention is not limited by the following description, and the present invention may be modified, as appropriate, and implemented using configurations other than those given below as examples within the spirit of the invention.

1. Definitions

In the present specification, a "halogen atom" means a fluorine atom, a chlorine atom, a bromine atom, or an iodine atom.

In the present specification, "alkyl" may be any aliphatic hydrocarbon group which is linear, branched, cyclic, or includes a combination thereof. The number of carbon atoms in the alkyl group is not particularly limited, and examples thereof include 1 to 20 carbon atoms ($C_{1-20}$), 3 to 15 carbon atoms ($C_{3-15}$), and 5 to 10 carbon atoms ($C_{5-10}$). When the number of carbon atoms is specified, this means "alkyl" having a number of carbon atoms in the range of the number. Examples of $C_{1-8}$ alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, and n-octyl. In the present specification, the alkyl group may have one or more arbitrary substituents. Examples of the substituent include, but are not limited to, an alkoxy group, a halogen atom, an amino group, mono- or di-substituted amino group, a substituted silyl group, or acyl. When the alkyl group has two or more substituents, they may be the same or different. The same applies to an alkyl moiety of other substituents containing an alkyl moiety (e.g., an alkoxy group, an arylalkyl group, and the like).

In the present specification, when a certain functional group is defined as "optionally substituted", a type of a substituent, a substitution position, and a number of substituents are not particularly limited, and when there are two or more substituents, they may be the same or different. Examples of the substituent include, but are not limited to, an alkyl group, an alkoxy group, a hydroxyl group, a carboxyl group, a halogen atom, a sulfo group, an amino group, an alkoxycarbonyl group, and an oxo group. Further substituents may be present on these substituents. Examples of such cases include, but are not limited to, a halogenated alkyl group and a dialkyl amino group.

In the present specification, "aryl" may be either a monocyclic or fused polycyclic aromatic hydrocarbon group, or may be an aromatic heterocyclic ring containing one or more hetero atoms (e.g., an oxygen atom, a nitrogen atom, or a sulfur atom, etc.) as a ring-constituting atom. In this case, this may be referred to as "heteroaryl" or "heteroaromatic". Even when the aryl is either a monocyclic or fused ring, it may be bonded in all possible positions. Non-limiting examples of monocyclic aryl include a phenyl group (Ph), a thienyl group (2- or 3-thienyl group), a pyridyl group, a furyl group, a thiazolyl group, an oxazolyl group, a pyrazolyl group, a 2-pyrazinyl group, a pyrimidinyl group, a pyrrolyl group, an imidazolyl group, a pyridazinyl group, a 3-isothiazolyl group, a 3-isoxazolyl group, a 1,2,4-oxadiazol-5-yl group, or a 1,2,4-oxadiazole-3-yl group. Non-limiting examples of fused polycyclic aryl include a 1-naphthyl group, a 2-naphthyl group, a 1-indenyl group, a 2-indenyl group, a 2,3-dihydroinden-1-yl group, a 2,3-dihydroinden-2-yl group, a 2-anthryl group, an indazolyl group, a quinolyl group, an isoquinolyl group, a 1,2-dihydroisoquinolyl group, a 1,2,3,4-tetrahydroisoquinolyl group, an indolyl group, an isoindolyl group, a phthalazinyl group, a quinoxalinyl group, a benzofuranyl group, a 2,3-dihydrobenzofuran-1-yl group, a 2,3-dihydrobenzofuran-2-yl group, a 2,3-dihydrobenzothiophene-1-yl group, a 2,3-dihydrobenzothiophene-2-yl group, a benzothiazolyl group, a benzimidazolyl group, a fluorenyl group, or a thioxanthenyl group. In the present specification, the aryl group may have one or more arbitrary substituents on the ring. Examples of the substituent include, but are not limited to, an alkoxy group, a halogen atom, an amino group, mono- or di-substituted amino group, a substituted silyl group, or acyl. When the aryl group has two or more substituents, they may be the same or different. The same applies to an aryl moiety of other substituents containing an aryl moiety (e.g., an aryloxy group, an arylalkyl group, and the like).

In the present specification, an "alkoxy group" is a structure in which the alkyl group is bonded to an oxygen atom, and examples thereof include a saturated alkoxy group which is linear, branched, cyclic, or a combination thereof. Preferred examples thereof include a methoxy group, an ethoxy group, a n-propoxy group, an isopropoxy group, a cyclopropoxy group, a n-butoxy group, an isobutoxy group, a s-butoxy group, a t-butoxy group, a cyclobutoxy group, a cyclopropylmethoxy group, a n-pentyloxy group, a cyclopentyloxy group, a cyclopropylethyloxy group, a cyclobutylmethyloxy group, a n-hexyloxy group, a cyclohexyloxy group, a cyclopropyl propyloxy group, a cyclobutylethyloxy group, or a cyclopentylmethyloxy group.

"Amide" as used in the present specification includes both RNR'CO— (in the case of R=alkyl, arylaminocarbonyl-) and RCONR'— (in the case of R=alkyl, alkylcarbonyl amino-).

"Ester" as used in the present specification includes both ROCO— (in the case of R=alkyl, alkoxycarbonyl-) and RCOO— (in the case of R=alkyl, alkylcarbonyloxy-).

In the present specification, the term "ring structure" means a heterocyclic or carbocyclic group when formed by a combination of two substituents, and such groups may be saturated, unsaturated, or aromatic. Therefore, cycloalkyl, cycloalkenyl, aryl, and heteroaryl as defined above are included. Examples include cycloalkyl, phenyl, naphthyl, morpholinyl, piperidinyl, imidazolyl, pyrrolidinyl, and pyridyl. In the present specification, substituents may form a ring structure with another substituent, and when such substituents are bonded to each other, a person skilled in the art can understand that a bond to a specific substitution, e.g., hydrogen, is formed. Therefore, when it is described that particular substituents together form a ring structure, a person skilled in the art can understand that the ring structures can be formed by normal chemical reactions and are readily generated. Any such ring structures and formation processes thereof are within the purview of a person skilled in the art.

2. Intracellularly-Retainable Red Fluorescent Probe

The intracellularly-retainable red fluorescent probe of the present invention, in one aspect thereof, contains a compound having a structure represented by the following general formula (I) or a salt thereof.

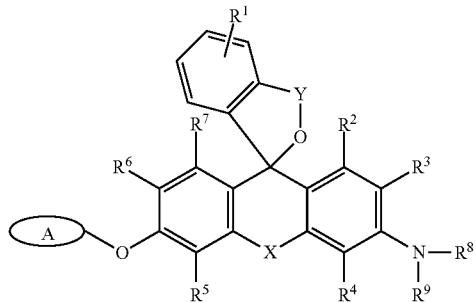

(I)

In the above general formula (I), $R^1$ represents a hydrogen atom, or one to four substituents bonded to a benzene ring. Examples of the substituent include, but are not limited to, an alkyl group, an alkoxy group, a halogen atom, an amino group, a mono- or di-substituted amino group, a substituted silyl group, or an acyl group. These substituents may be further substituted with one or more substituents. Examples of the substituents include one or two or more of an alkyl group, an alkoxy group, a halogen atom, a hydroxyl group, a carboxyl group, an amino group, and a sulfo group and the like. When there are two or more substituents on the benzene ring, the substituents may be the same or different. $R^1$ is more preferably a hydrogen atom, a lower alkyl group, or a lower alkoxy group. A hydrogen atom is particularly preferred.

$R^3$, $R^4$, $R^5$, and $R^6$ each independently represent —$CFR^{10}R^{11}$, —$CF_2R^{12}$, a hydrogen atom, a hydroxyl group, an alkyl group, or a halogen atom (the alkyl group may be substituted). $R^{10}$, $R^{11}$, and $R^{12}$ each independently represent a hydrogen atom, an alkyl group, or an alkenyl group. Furthermore, at least one of $R^3$, $R^4$, $R^5$, and $R^6$ represents —$CFR^{10}R^{11}$ or —$CF_2R^{12}$. At least one of $R^3$, $R^4$, $R^5$, and $R^6$ is preferably —$CFR^{10}R^{11}$. At least one of $R^3$, $R^4$, $R^5$, and $R^6$ is more preferably —$CH_2F$.

$R^2$ and $R^7$ each independently represent a hydrogen atom, a hydroxyl group, an alkyl group, or a halogen atom. Both $R^2$ and $R^7$ are preferably hydrogen atoms.

$R^8$ and $R^9$ each independently represent a hydrogen atom or an alkyl group. When both $R^8$ and $R^9$ represent alkyl groups, the alkyl groups may be the same or different. For example, $R^8$ and $R^9$ are preferably each independently a methyl group or an ethyl group, and a case in which any of $R^8$ and $R^9$ is an ethyl group is more preferred.

X represents $Si(R^a)(R^b)$. Here, $R^a$ and $R^b$ each independently represent a hydrogen atom or an alkyl group, and the alkyl group is preferably an alkyl group having 1 to 5 carbon atoms, which may be substituted. Preferably, both $R^a$ and $R^b$ are hydrogen atoms.

Y is —C(=O)— or —$R^cC$(=O)—. Here, $R^c$ is an alkylene group having 1 to 3 carbon atoms. The alkylene group may be a straight-chain alkylene group or a branched-chain alkylene group. For example, a methylene group (—$CH_2$—), an ethylene group (—$CH_2$—$CH_2$—), or a propylene group (—$CH_2$-$CH_2$-$CH_2$—) may be used, as well as —CH($CH_3$)—, —$CH_2$-CH($CH_3$)—, —CH($CH_2CH_3$)—, and the like as a branched-chain alkylene group. Preferably, Y is —C(=O)—.

A group A represents a monovalent group which is cleaved by an enzyme, and specific examples thereof include, but are not limited to, a β-galactopyranosyl group, an α-mannosyl group, a β-N-acetylglucosamyl group, a β-lactam group, a phosphoric acid ester, an aminophenoxy group, a hydroxyphenoxy group, and γ-glutamic acid.

Examples of an enzyme for cleaving the group A include a reductase, an oxidase, or a hydrolase, and a reporter enzyme or an enzyme specifically expressed or activated in cancer cells. More specifically, examples thereof include, but are not limited to, β-galactosidase, β-lactamase, α-mannosidase, esterase, alkali phosphatase, luciferase, peroxidase, cytochrome P450 oxidase, β-glucosidase, β-glucuronidase, β-hexosaminidase, lactase, and γ-glutamyl transferase. β-galactosidase, β-lactamase, alkali phosphatase, luciferase, β-hexosaminidase, peroxidase, or γ-glutamyltransferase is preferred. β-galactosidase is most preferred.

The compound represented by the above formula (I) may exist as a salt. Examples of the salt include a base addition salt, an acid addition salt, and an amino acid salt. Examples of the base addition salt include metal salts such as a sodium salt, a potassium salt, a calcium salt, and a magnesium salt; an ammonium salt; or organic amine salts such as a triethylamine salt, a piperidine salt, and a morpholine salt. Examples of the acid addition salt include mineral acid salts such as a hydrochloride, a sulfate, and a nitrate; and salts of organic acids such as salts of methanesulfonic acid, p-toluenesulfonic acid, citric acid, and oxalic acid. Examples of the amino acid salt include a glycinate. The salt of the compound represented by the formula (I) of the present invention is not limited to these examples.

The compound represented by the formula (I) may have one or two or more asymmetric carbons, depending on the types of substituents, and a stereoisomer such as an optical isomer or a diastereomer may exist. Any of a stereoisomer in pure form, a mixture of stereoisomers, and a racemate thereof and the like is included in the scope of the present invention.

The compound represented by the formula (I) or the salt thereof may exist as a hydrate or a solvate, but these substances are both included in the scope of the present invention. Examples of the type of the solvent forming the solvate include, but are not particularly limited to, solvents such as ethanol, acetone, and isopropanol.

In Examples of the present specification, manufacturing methods are specifically described for representative compounds included as the compound represented by the formula (I), and a person skilled in the art can easily manufacture any compound included by the formula (I) by referring to the disclosure of the present specification and appropriately selecting starting materials or reagents, and reaction conditions and the like as needed.

Specific representative examples of the compound of the formula (I) which is used as the intracellularly-retainable red fluorescent probe of the present invention include the following compounds. The compound is not limited to these examples.

[Chemical Formula 3]

3. Mechanisms of Fluorescence Emission and Intracellular Retention of Fluorescent Probe of the Present Invention The mechanisms of fluorescence emission and intracellular retention in the intracellularly-retainable red fluorescent probe of the present invention will be described below.

When the intracellularly-retainable red fluorescent probe containing the compound represented by the formula (I) is taken into a cell, in a cell expressing an enzyme capable of cleaving the group represented by A, the group represented by A is cleaved in the cell, hydrogen fluoride is released from the $—CFR^{10}R^{11}$ or $—CF_2R^{12}$ positioned at $R^3$, $R^4$, $R^5$, or $R^6$, and a quinone methide is generated. Because the quinone methide is rapidly subjected to attack by surrounding nucleophiles, when a quinone methide is generated in the cell, the quinone methide rapidly reacts with nucleophilic groups of surrounding proteins, and is irreversibly bonded to the proteins.

For example, in the case of the compound ((A) in the formula) of the formula (Ia), β-galactosidase causes cleavage of the group A ((B) in the formula) and ring-opening of a spiro ring as described below, and a compound ((C) in the formula)) covalently bonded to an intracellular protein is generated. The detailed mechanism of the fluorescence emission by the ring opening of the spiro ring is described in International Publication 2005/024049.

[Chemical Formula 4]

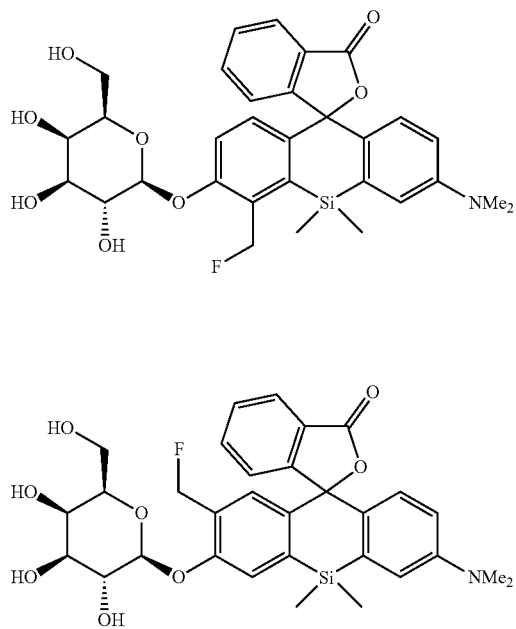

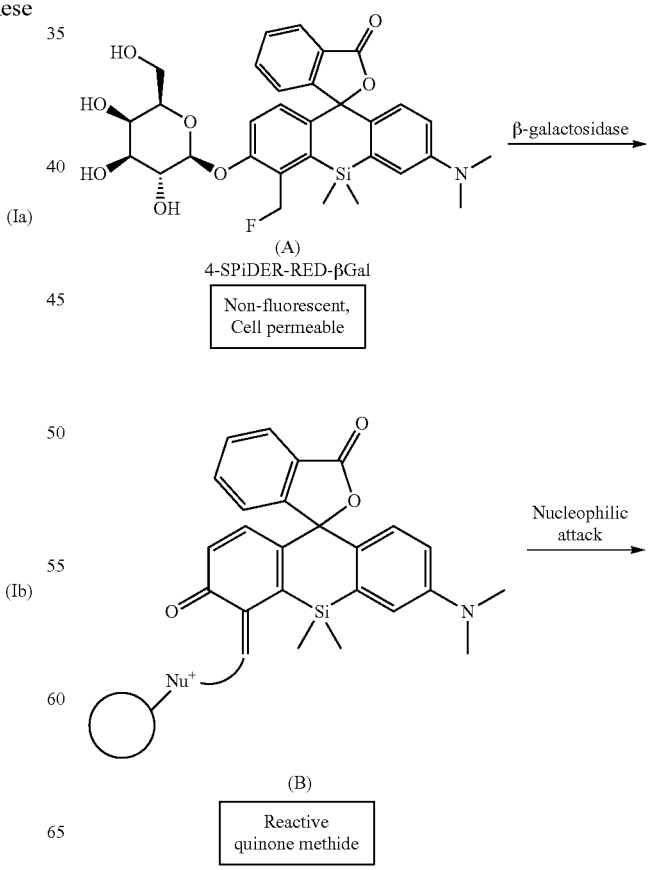

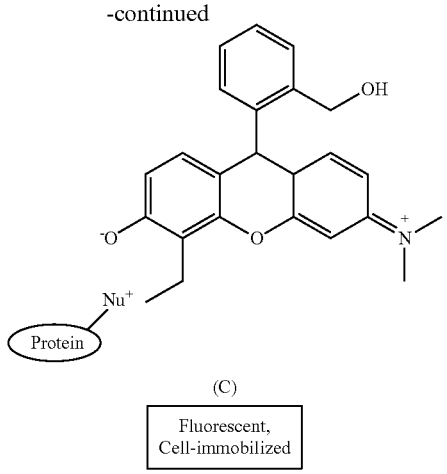

(C)

Fluorescent, Cell-immobilized

A compound represented by the formula (I) or a salt thereof exhibits almost no fluorescence when irradiated with excitation light in a neutral range, e.g., excitation light having a wavelength of about 500 to 650 nm, but a ring-opened compound formed by enzyme activity has the property of emitting extremely strong fluorescence under the same conditions. Therefore, when a cell having taken in the intracellularly-retainable red fluorescent probe represented by the formula (I) does not express an enzyme capable of cleaving the group A, the ring-opened compound of (C) is not generated, and a fluorescent substance is not generated in the cell. Thus, by using the intracellularly-retainable red fluorescent probe represented by the formula (I), fluorescence is selectively generated only in a cell expressing and activating an enzyme capable of cleaving the group represented by A. Furthermore, because the reaction product compound represented by (C) can be covalently bonded to an intracellular protein, leakage thereof to the outside of the cell is suppressed. This makes it possible to specifically visualize a cell expressing and activating the enzyme at a single-cell level of detail.

In the compound represented by the formula (I), a structure having a silicon atom at X which is a 10-position element of a xanthene ring and a substituent (Y—O moiety) based on a carboxyl group at a 2 position of a benzene ring is adopted, whereby red fluorescence having a fluorescence peak wavelength of 600 to 750 nm can be provided as fluorescence emission by ring opening of a spiro ring. As a result, the compound can be separated from the fluorescent signal of GFP (green fluorescent protein), which makes it possible to perform co-staining together with GFP.

From the characteristics described above, the compound represented by the formula (I) of the present invention makes it possible to visualize a cell at a single-cell level of detail without immobilization thereof or after immobilization thereof, and has a wide range of usage applications including use thereof as a tool for cell biological research in cell lines as a fluorescent probe performing co-staining together with GFP, as well as a test drug, a diagnostic drug, and the like used for rapid pathologic examination in surgical settings for cancer and the like.

4. Method for Selective Cell Visualization Using Intracellularly-Retainable Red Fluorescent Probe of the Present Invention The intracellularly-retainable red fluorescent probe of the present invention exhibits the characteristics described above, and can therefore be used in a method for cell-specific visualization of a target cell expressing a specific enzyme. Specifically, a step is performed for bringing the intracellularly-retainable red fluorescent probe containing the compound of the formula (I) or a salt thereof into contact with the enzyme such as β-galactosidase specifically expressed in a target cell, and a step is then performed for detecting fluorescence which occurs in response to excitation light irradiation, whereby only the target cell expressing the β-galactosidase and the like can be specifically visualized as a red fluorescence signal.

Representative examples of means for bringing the intracellularly-retainable red fluorescent probe of the present invention into contact with the enzyme specifically expressed in the target cell include sample addition, coating, or spraying of a solution including the intracellularly-retainable red fluorescent probe, but the means can be selected as appropriate for the application. When the intracellularly-retainable red fluorescent probe of the present invention is applied for diagnosis or assisting in diagnosis in an animal individual, or for detecting a specific cell or tissue therein, the means for bringing the compound into contact with the enzyme expressed in the target cell or tissue is not particularly limited, and for example, administration means common in the relevant field such as intravenous administration may be used.

Photoirradiation of the target cell may be performed by radiating light directly or via a waveguide (optical fiber and the like) to the target cell. Any light source can be used, which is capable of radiating light which includes the wavelength absorbed by the intracellularly-retainable red fluorescent probe of the present invention after enzymatic cleavage thereof, and the light source can be appropriately selected in accordance with factors such as the environment in which the method of the present invention is performed.

The intracellularly-retainable red fluorescent probe of the present invention may be used without modification as the compound represented by the above general formula (I) or a salt thereof, or may, as needed, be used as a composition obtained by blending additives normally used for preparing reagents. For example, additives such as a solubilizer, a pH adjuster, a buffer agent, and an isotonizing agent, for using a reagent in a physiological environment can be used, and the blended amounts of these additives can appropriately be selected by a person skilled in the art. These compositions are commonly provided in an appropriate form of the composition such as a mixture in a powder form, a freeze-dried product, granules, a tablet, or a liquid, but the compositions can be dissolved for application in distilled water for injection or an appropriate buffer solution at the time of use.

EXAMPLES

Hereinafter, the present invention will be described in more detail with reference to Examples, but the present invention is not limited by these Examples.

In the present Examples, the following apparatus and conditions were used.

NMR measurement was carried out using ULTRA-SHIELD 400 (BRUKER). (400 MHz for $^1$H NMR, 100 MHz for $^{13}$C NMR)

Silica gel 60N (spherical, neutral, KANTO CHEMICAL Co., Inc.) was used for silica gel column chromatography.

The following apparatuses and column were used for purification by reversed phase HPLC.

Pump: PU-2080 and PU-2087 (JASCO Corporation)
Detector: MD-2010 (JASCO Corporation)
Column: Inertsil ODS-3 (20×250 mm, GL Science Inc.)

The following solvents A and B were used for purification by reverse phase HPLC.

A: 100 mM triethylamine acetate
B: 99% acetonitrile, 1% milliQ

Ultraviolet-visible absorption spectroanalysis and fluorescence spectroanalysis were using Shimadzu UV-2450 (Shimadzu Corporation) and Hitachi F-7000 (Hitachi, Ltd.).

Fluorescence imaging experiments were performed using a confocal fluorescence microscope TCS SPSX (Leica) and an objective lens HCX PL APO CS 40×/1.25 (Leica).

Example 1

1. Synthesis of Probe Molecule

4-$CH_2$F-SPiDER-RED-βGal and 2-$CH_2$F-SPiDER-RED-βGal used as an intracellularly-retainable red fluorescent probe of the present invention were synthesized as shown below.

(1) Synthesis of 4-$CH_2$F-SPiDER-RED-βGal

According to the following scheme, 4-$CH_2$F-SPiDER-RED-βGal which was the intracellularly-retainable red fluorescent probe of the present invention was synthesized.

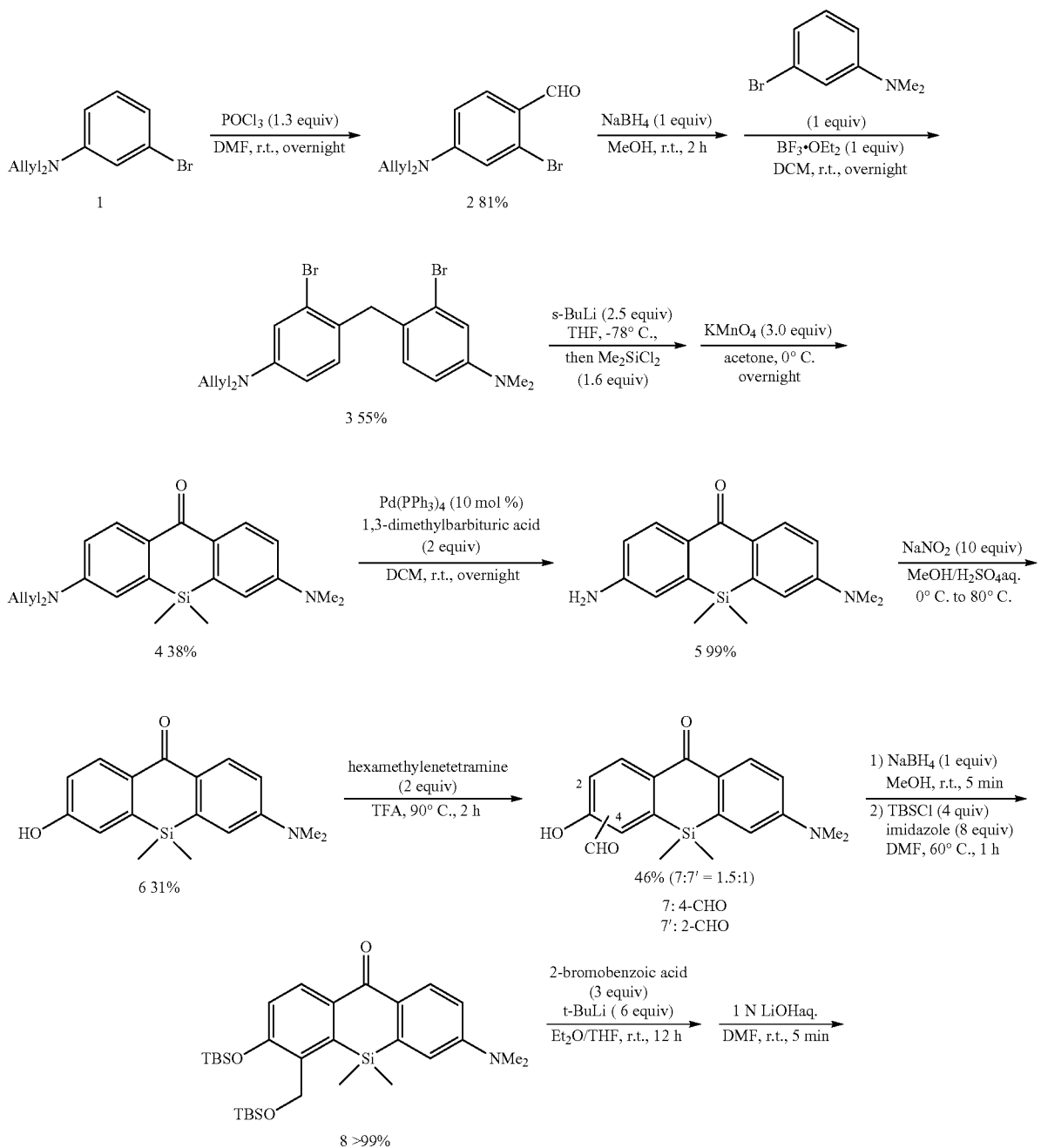

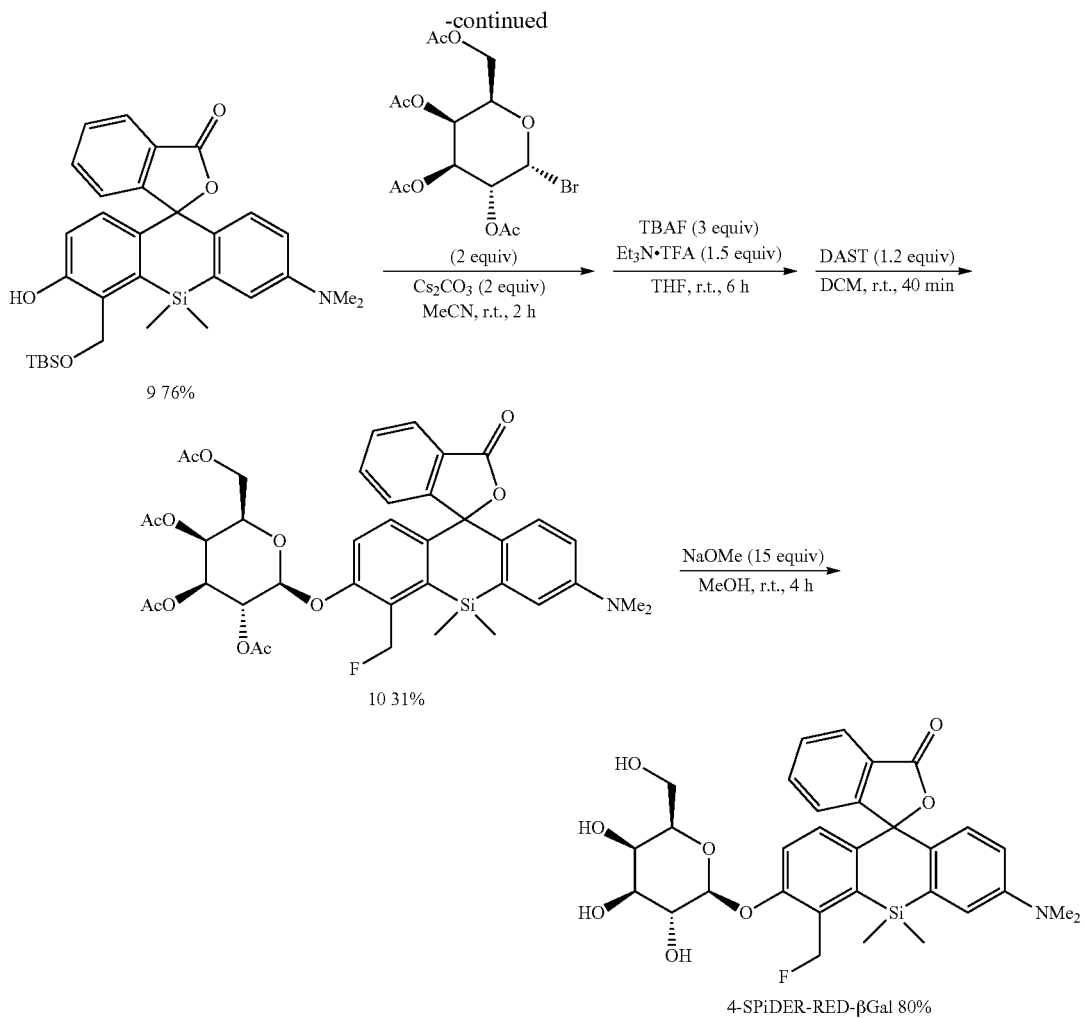

10 31%

4-SPiDER-RED-βGal 80%

[Synthesis of Compound 1]

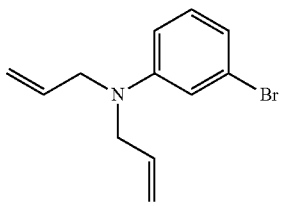

A compound 1 was synthesized in accordance with the previously reported literature (Chemical Communications 47, 4162-4164 (2011)). Specifically, 3-bromoaniline (4.0 mL, 37 mmol) and allyl bromide (11 mL, 131 mmol) were dissolved in MeCN (40 mL) to obtain a dissolved product, to which potassium carbonate (11 g, 80 mmol) was then added. The reaction solution was stirred overnight at 80° C. under an argon atmosphere. After the reaction solution was cooled to room temperature, an insoluble matter was removed by Celite filtration to obtain a filtrate, and the filtrate was removed under reduced pressure to obtain an oily substance. The oily substance was purified by silica gel column chromatography (eluent:AcOEt:hexane=2.5:97.5 to AcOEt:hexane=10:90) to obtain the desired compound 1 as a transparent oily substance (8.6 g, 93%).

1H-NMR (300 MHz, CDCl3) δ 3.89-3.90 (4H, m), 5.12-5.16 (2H, m), 5.19 (2H, m) 5.76-5.89 (2H, m), 6.57-6.61 (1H, m), 6.77-6.81 (2H, m), 7.03 (1H, t, J=8.1 Hz).

[Synthesis of Compound 2]

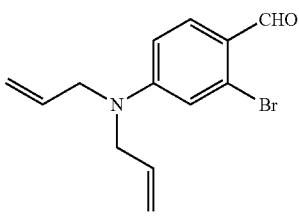 [SMILES: C=CCN(CC=C)c1ccc(C=O)c(Br)c1]

The compound 1 (1.0 g, 4.0 mmol) was dissolved in DMF (3 mL) to obtain a dissolved product, to which phosphoryl chloride (490 μL, 5.2 mmol) was then added. The reaction solution was stirred overnight under an argon atmosphere, and 2N NaOH aq was then added dropwise to the reaction solution, followed by performing liquid separating extraction using $CH_2Cl_2$. The collected organic layer was removed under reduced pressure to obtain an oily substance, and the oily substance was further dissolved in AcOEt to obtain a dissolved product. The dissolved product was washed three times with a saturated $NH_4Cl$ aqueous solution. The collected organic layer was dried over anhydrous sodium sulfate, and removed under reduced pressure to obtain a residue. The residue was purified by medium pressure silica gel column chromatography (eluent:$CH_2Cl_2$:hexane=67:33 to 100:0) to obtain a compound 2 (902 mg, 81%).

1H-NMR (300 MHz, CDCl3) δ 3.98-3.99 (4H, m), 5.15-5.23 (4H, m), 5.81-5.85 (2H, m), 6.64 (1H, dd, J=8.8 Hz, 2.2 Hz), 6.81 (1H, d, J=2.9 Hz), 7.77 (1H, d, J=8.8 Hz), 10.07 (1H, s) 13C-NMR (75 MHz, CDCl3) δ 52.7, 111.0, 115.2, 117.0, 122.4, 129.7, 131.1, 131.6, 153.5, 190.1

[Synthesis of Compound 3]

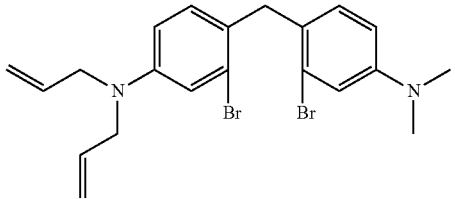 [SMILES: C=CCN(CC=C)c1ccc(Cc2ccc(N(C)C)cc2Br)c(Br)c1]

The compound 2 (3.6 g, 13 mmol) was dissolved in MeOH (15 mL) to obtain a dissolved product, to which sodium borohydride was slowly added. The reaction solution was stirred at room temperature under an argon atmosphere for 2 hours. The reaction solution was diluted with a saturated $NaHCO_3$ aqueous solution, followed by performing liquid separating extraction twice using $CH_2Cl_2$. The collected organic layer was dried over anhydrous sodium sulfate, and removed under reduced pressure to obtain an oily substance (2.9 g, 10 mmol). The oily substance was dissolved in $CH_2Cl_2$ (30 mL). 3-bromo-N,N,-dimethylaniline (1.4 mL, 10 mmol) and boron trifluoride ethyl ether complex (1.7 mL, 13 mmol) were added to the dissolved product, followed by stirring at room temperature overnight under an argon atmosphere. The reaction solution was diluted with a saturated $NaHCO_3$ aqueous solution, followed by performing liquid separating extraction twice using $CH_2Cl_2$. The collected organic layer was dried over anhydrous sodium sulfate. The organic layer was removed under reduced pressure to obtain a residue, and the residue was purified by medium pressure silica gel column chromatography (eluent: $CH_2Cl_2$:hexane=0:100 to 50:50) to obtain a compound 3 (3.2 g, 55%).

$^1$H-NMR (300 MHz, CDCl$_3$) δ 2.91 (6H, s), 3.87 (4H, d, J=5.1 Hz), 3.98 (2H, s), 5.16 (4H, dd, J=1.8, 13.6 Hz), 5.78-5.87 (2H, m), 6.54 (1H, dd, J=8.8 Hz, 2.9 Hz), 6.59 (1H, dd, J=8.8 Hz, 2.9 Hz), 6.79 (1H, d, J=8.8 Hz), 6.87 (1H, d, J=8.1 Hz), 6.90 (1H, d, J=2.2 Hz), 6.93 (1H, d, J=2.9 Hz)$^{13}$C-NMR (75 MHz, CDCl$_3$) δ39.8, 40.5, 52.7, 111.6, 111.8, 115.9, 116.2, 116.2, 125.5, 125.6, 126.8, 127.0, 130.7, 130.8, 133.4, 148.1, 150.0

[Synthesis of Compound 4]

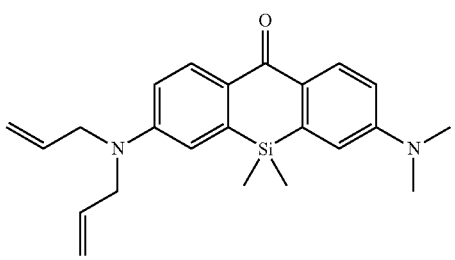 [SMILES: C=CCN(CC=C)c1ccc2c(c1)[Si](C)(C)c1cc(N(C)C)ccc1C2=O]

The compound 3 (3.3 g, 7.1 mmol) was dissolved in THF (15 mL) to obtain a dissolved product, and the dissolved product was stirred at −78° C. for 20 min under an argon atmosphere. After s-BuLi (18 mL, 18 mmol) was added dropwise to the reaction solution, the mixture was stirred for 30 minutes under an argon atmosphere at −78° C. to obtain a reaction solution, to which dichlorodimethylsilane (1.3 mL, 11 mmol) was further added. The reaction solution was gradually returned to room temperature, and further stirred at room temperature under an argon atmosphere for 2 hours. After 2N hydrochloric acid was added dropwise to the reaction solution, a saturated $NaHCO_3$ aqueous solution was added to the reaction solution, followed by performing liquid separating extraction three times using $CH_2Cl_2$. The collected organic layer was dried over anhydrous sodium sulfate, and removed under reduced pressure to obtain an oily residue. The residue was dissolved in acetone (30 mL) to obtain a dissolved product, and the dissolved product was cooled to 0° C., followed by adding potassium manganite (VII) to the cooled dissolved product. After the mixture was stirred at 0° C. for 3 hours, 3 equivalents of potassium manganite (VII) (3.4 g, 21 mmol) was further added to the reaction solution, and the reaction solution was gradually returned to room temperature. After the reaction solution was stirred at room temperature overnight, an insoluble matter was subjected to Celite filtration to obtain a filtrate. The filtrate was removed under reduced pressure to obtain a residue, and the residue was purified by medium pressure silica gel column chromatography (eluent:AcOEt:$CH_2Cl_2$=0:100 to 10:90) to obtain a compound 4 as a yellow solid (1.0 g, 38%).

$^1$H-NMR (300 MHz, CDCl$_3$) δ 0.44 (6H, s), 3.10 (6H, s), 4.03 (4H, d, J=5.1 Hz), 5.17-5.20 (2H, m), 5.23 (2H, br), 5.84-5.93 (2H, m), 6.77-6.85 (4H, m), 8.37 (2H, t, J=9.5 Hz)$^{13}$C-NMR (75 MHz, CDCl$_3$) δ −1.1, 40.0, 52.7, 113.1, 113.4, 114.2, 114.7, 116.5, 129.7, 130.0, 131.6, 133.0, 140.4, 140.4, 150.1, 151.4, 185.1 HRMS (ESI$^+$): calcd for [M+H]$^+$, 377.20491; found, 377.20176 (−3.15 mmu).

[Synthesis of Compound 5]

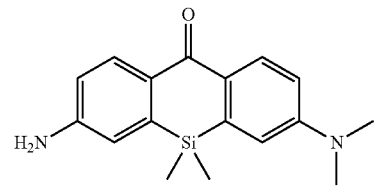 [SMILES: CN(C)c1ccc2c(c1)[Si](C)(C)c1cc(N)ccc1C2=O]

The compound 4 (1.0 g, 2.7 mmol) was dissolved in $CH_2Cl_2$ (35 mL) to obtain a dissolved product, to which tetrakis(triphenylphosphine)palladium(0) (0.31 g, 0.27 mmol) and 1,3-dimethylbarbituric acid (0.86 g, 5.4 mmol) were added. The mixture was stirred overnight at room temperature under an argon atmosphere. The reaction solution was extracted three times with a saturated $Na_2CO_3$ aqueous solution, followed by drying over anhydrous sodium sulfate and removing under reduced pressure, to obtain a residue. The residue was purified by medium pressure silica gel column chromatography (eluent:AcOEt:hexane=45:55 to 67:33) to obtain a compound 5 (790 mg, 99%).

$^1$H-NMR (300 MHz, CD$_3$OD) δ 0.42 (6H, s), 3.06 (6H, s), 6.74-6.89 (4H, m), 8.14 (1H, d, J=8.8 Hz), 8.22 (1H, d, J=8.8 Hz)$^{13}$C-NMR (75 MHz, CD$_3$OD) δ −1.2, 40.1, 114.1, 115.6, 116.6, 118.4, 129.9, 130.9, 132.5, 132.7, 142.2, 142.7, 153.1, 153.3, 187.5 HRMS (ESI⁺): calcd for [M+H]⁺, 297.14231; found, 297.14250 (0.19 mmu)

[Synthesis of Compound 6]

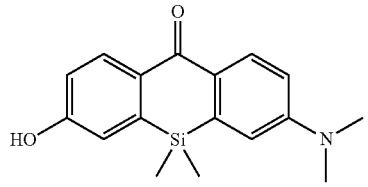 [SMILES: CN(C)c1ccc2c(c1)[Si](C)(C)c1cc(O)ccc1C2=O]

The compound 5 (258 mg, 0.87 mmol) was dissolved in a mixed solvent of MeOH (10 mL) and 6N sulfuric acid (25 mL) to obtain a dissolved product, and the dissolved product was cooled to 0° C. Sodium nitrile (600 mg, 8.7 mmol) dissolved in H$_2$O (4 mL) was added dropwise to the dissolved product over 1 hour, and the mixture was then added portionwise to heated 1 N sulfuric acid (100 mL). After the mixture was stirred for 10 minutes, the reaction solution was returned to room temperature, and the reaction solution was subjected to liquid separating extraction four times using CH$_2$Cl$_2$. The collected organic layer was dried over anhydrous sodium sulfate, and removed under reduced pressure to obtain a residue. The residue was purified by medium pressure silica gel column chromatography (eluent:AcOEt:CH$_2$Cl$_2$=0:100 to 10:90) to obtain a compound 6 (81 mg, 31%).

¹H-NMR (300 MHz, CD$_3$OD) δ 0.44 (6H, s), 3.09 (6H, s), 6.84-6.89 (2H, m), 6.93 (1H, dd, J=8.8 Hz, 2.2 Hz), 7.06 (1H, d, J=2.2 Hz), 8.21-8.26 (2H, m)¹³C-NMR (75 MHz, CD$_3$OD) δ−1.3, 40.1, 114.2, 115.6, 118.2, 120.0, 129.6, 132.8, 133.0, 134.1, 142.3, 143.2, 153.5, 161.9, 187.6 HRMS (ESI⁺): calcd for [M+H]⁺, 298.12633; found, 298.12254 (−3.79 mmu).

[Synthesis of Compound 7]

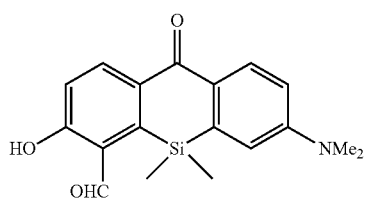 [SMILES: CN(C)c1ccc2c(c1)[Si](C)(C)c1c(ccc(O)c1C=O)C2=O]

The compound 6 (1.45 mmol, 431 mg) and hexamethylenetetramine (2.9 mmol, 406 mg) were heated in TFA (2.5 mL) at 90° C. for 3 hours. 1N Hydrochloric acid was added to the heated product, and the mixture was further stirred at room temperature for 1 hour. Then, the reaction solution was neutralized with a sodium hydroxide aqueous solution, and ethyl acetate was added thereto, followed by performing liquid separating operation three times. The obtained organic layer was dried over anhydrous sodium sulfate, and a solvent was removed with an evaporator. By purification using silica gel column chromatography (Hexane/CH$_2$Cl$_2$/EtOAc=1/1/0.25), a desired compound 7 was obtained as a yellow solid (130 mg, 28%). An isomeric compound 7' was also obtained simultaneously (87 mg, 18%).

¹H NMR (300 MHz, CDCl$_3$) δ12.25 (1H, s), 10.45 (1H, s), 8.75 (1H, d, J=9.5 Hz), 8.37 (1H, d, J=8.8 Hz), 7.17 (1H, d, J=8.8 Hz), 6.89 (1H, dd, J=9.2 Hz, 2.6 Hz), 6.80 (1H, d, J=2.2 Hz), 3.14 (6H, s), 0.67 (6H, s); ¹³C NMR (100 MHz, CDCl$_3$) δ196.0, 184.0, 165.9, 152.1, 145.3, 139.6, 139.0, 134.5, 131.7, 127.4, 122.4, 120.2, 113.7, 113.6, 40.0, 1.6

[Synthesis of Compound 8]

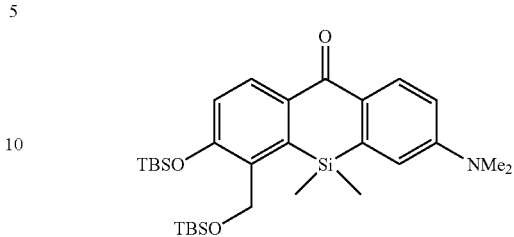

The compound 7 (0.76 mmol, 247 mg) was dissolved in MeOH (5 mL) to obtain a dissolved product, to which NaBH$_4$ (0.76 mmol, 29 mg) was added at room temperature. In five minutes, a saturated aqueous solution of ammonium chloride was added to the mixture, followed by stirring. Then, ethyl acetate was added to the reaction solution, followed by performing liquid separating operation three times. The obtained organic layer was dried over anhydrous sodium sulfate, and a solvent was removed with an evaporator. TBSCl (3 mmol, 452 mg), imidazole (6 mmol, 408 mg), and DMF (1 mL) were added thereto, and the mixture was stirred at 60° C. for 1 hour. After the reaction, water was added to the reaction solution, followed by performing liquid separating operation three times using hexane. The obtained organic layer was dried over anhydrous sodium sulfate, and a solvent was removed with an evaporator. The obtained compound was purified by silica gel column chromatography (Hexane/EtOAc=10/1) to obtain a desired compound as a pale yellow viscous liquid (422 mg, 99%).

¹H NMR (300 MHz, CDCl$_3$) δ8.38 (1H, d, J=8.8 Hz), 8.28 (1H, dd, J=8.8 Hz, 1.5 Hz), 6.98 (1H, d, J=8.1 Hz), 6.80-6.83 (2H, m), 4.92 (2H, s), 3.10 (6H, s), 1.02 (9H, s), 0.90 (9H, s), 0.60 (6H, s), 0.28 (6H, s), 0.16 (6H, s); ¹³C NMR (100 MHz, CDCl$_3$) δ186.4, 156.2, 151.9, 143.2, 141.0, 136.3, 135.1, 1331.3, 128.8, 120.5, 113.8, 113.2, 59.2, 40.0, 26.2, 26.1, 18.6, 18.6, 0.6, −3.7, −4.7; HRMS (ESI) exact mass calcd. for: m/z 556.30985 ([M+H]⁺), found: m/z 556.30757 (−2.28 mmu).

[Synthesis of Compound 9]

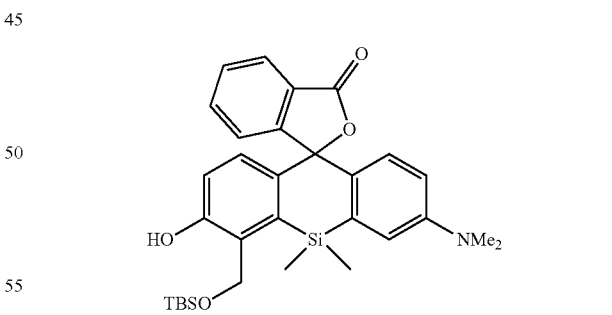

2-bromobenzoic acid (2 mmol, 402 mg) was dissolved in Et$_2$O (10 mL) to obtain a dissolved product, to which t-BuLi (1.7 M in pentane, 6 mmol, 3.5 mL) was added at −78° C. At this temperature, the mixture was stirred for 3 hours. Using a cannula, this solution was added dropwise to another flask containing a THF solution (3 mL) of the compound 8 (0.6 mmol, 331 mg) at −78° C. After the dropwise addition, the mixture was stirred at room temperature for 12 hours, and 1N hydrochloric acid was added to the reaction solution. The mixture was further stirred for 30 minutes. Thereafter, the reaction solution was neutralized with a sodium bicarbonate aqueous solution, and hexane was added thereto, followed by performing liquid separating operation three times. The obtained organic layer was dried over anhydrous sodium sulfate, and a solvent was removed with an evaporator. The remaining crude product was dissolved in DMF (6 mL) to obtain a dissolved product, and 1N LiOH (2 mL) was added to the dissolved product at room temperature. After the mixture was stirred for 5 minutes, a saturated aqueous solution of ammonium chloride was added to the reaction solution, and the mixture was extracted three times with a mixed solvent of hexane/AcOEt=3/1. The obtained organic layer was dried over anhydrous sodium sulfate, and a solvent was removed with an evaporator. The obtained compound was purified by silica gel column chromatography (hexane/$CH_2Cl_2$=½, 2% AcOEt) to obtain a desired compound as a colorless viscous liquid (252 mg, 76%).

$^1$H NMR (400 MHz, $CDCl_3$) δ8.62 (1H, s), 7.94 (1H, d, J=8.0 Hz), 7.60 (1H, t, J=7.6 Hz), 7.50 (1H, t, J=7.6 Hz), 7.22 (1H, d, J=7.6 Hz), 6.90-6.92 (2H, m), 6.82 (1H, d, J=9.6 Hz), 6.76 (1H, d, J=8.0 Hz), 6.59 (1H, d, J=9.6 Hz), 5.21 (1H, d, J=12 Hz), 5.17 (1H, d, J=12 Hz), 2.96 (6H, s), 0.97 (9H, s), 0.71 (3H, s), 0.66 (3H, s), 0.42 (6H, s); $^{13}$C NMR (100 MHz, $CDCl_3$) δ170.9, 157.0, 155.3, 149.6, 136.4, 135.6, 134.1, 133.4, 131.1, 129.1, 128.8, 128.6, 128.0, 126.1, 125.9, 124.2, 119.0, 116.2, 114.1, 91.8, 66.5, 40.4, 25.9, 18.3, 14.4, 1.4, −5.1; HRMS (ESI) exact mass calcd. for $C_{31}H_{39}NO_4Si_2$: m/z 546.24904 ([M+H]$^+$), found: m/z 546.25315 (+4.1 mmu).

[Synthesis of Compound 10]

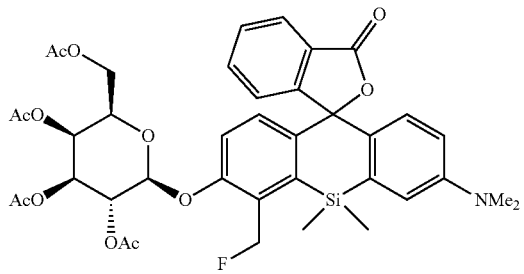 [SMILES: CC(=O)OC[C@H]1O[C@@H](Oc2ccc3c(c2CF)[Si](C)(C)c2cc(N(C)C)ccc2C32OC(=O)c3ccccc32)[C@H](OC(C)=O)[C@@H](OC(C)=O)[C@H]1OC(C)=O]

The compound 9 (0.46 mmol, 252 mg), 2,3,4,6-tetra-O-acetyl-α-D-galactopyranosyl bromide (0.92 mmol, 379 mg), and $Cs_2CO_3$ (0.92 mmol, 300 mg) were stirred in MeCN (3 mL) at room temperature for 2 hours. A saturated aqueous solution of ammonium chloride was added to the reaction solution, and the mixture was extracted three times with ethyl acetate. The obtained organic layer was dried over anhydrous sodium sulfate, and a solvent was removed with an evaporator. The remaining crude product was dissolved in THF (5 mL) to obtain a dissolved product, to which $Et_3N$ (0.8 mmol, 0.11 mL) and TFA (0.8 mmol, 60 μL) were added. Then, TBAF (1M in THF, 1.5 mmol, 1.5 mL) was added to the mixture, followed by stirring at room temperature for 6 hours. After the completion of the reaction was confirmed by TLC, an ammonium chloride aqueous solution was added to the reaction solution, and the mixture was extracted three times with ethyl acetate. The obtained organic layer was dried over anhydrous sodium sulfate, and a solvent was removed with an evaporator. After most impurities were removed by silica gel column chromatography ($Et_2O$) to obtain a crude product, the crude product was dissolved in $CH_2Cl_2$ (5 mL) to obtain a dissolved product, to which DAST (0.36 mmol, 48 μL) was added at 0° C. After the mixture was stirred for 30 minutes, an ammonium chloride aqueous solution was added to the reaction solution, and the mixture was extracted three times with $CH_2Cl_2$. The obtained organic layer was dried over anhydrous sodium sulfate, and a solvent was removed with an evaporator. By purification using silica gel column chromatography ($CH_2Cl_2$/$Et_2O$=10/1), a desired compound was obtained as a 1:1 diastereoisomeric mixture in a yield of 31% (110.4 mg).

$^1$H NMR (400 MHz, $CDCl_3$, dr=1:1) δ7.95 (2H, d, J=7.6 Hz), 7.61 (2H, t, J=7.6 Hz), 7.51 (2H, t, J=7.6 Hz), 7.22 (2H, t, J=7.6 Hz), 7.10 (2H, t, J=9.2 Hz), 6.94-7.00 (4H, m), 6.87 (2H, dd, J=9.2 Hz, 2.8 Hz), 6.60 (2H, d, J=9.2 Hz, 2.8 Hz), 5.81 (1H, t, J=10.4 Hz), 5.69 (1H, t, J=10.4 Hz), 5.56 (2H, d, J=10.4 Hz, 8.0 Hz), 5.42-5.46 (2H, m), 5.09 (2H, td, J=9.6 Hz, 3.2 Hz), 5.02 (1H, d, J=8.0 Hz), 4.97 (1H, d, J=8.0 Hz), 4.01-4.22 (8H, m), 2.98 (12H, s), 1.97-2.19 (24H, m), 0.79 (3H, s), 0.75 (3H, s), 0.72 (3H, s), 0.66 (3H, s); HRMS (ESI) exact mass calcd. for $C_{39}H_{43}FNO_{12}Si$: m/z 764.25445 ([M+H]$^+$), found: m/z 764.25794 (+3.5 mmu).

[Synthesis of 4-$CH_2$F-SPiDER-RED-βGal]

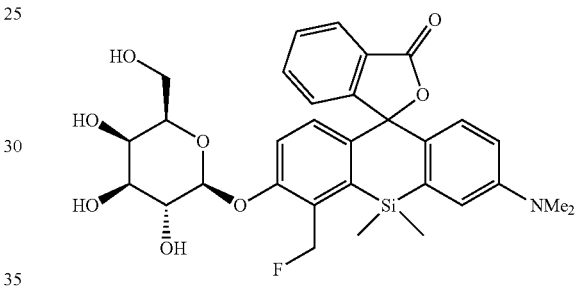

A compound 10 (0.15 mmol, 114 mg) was dissolved in MeOH (3 mL) to obtain a dissolved product, to which NaOMe (2.3 mmol, 124 mg) was added. The mixture was stirred at room temperature for 3 hours. After the reaction solution was neutralized by adding AcOH (2.3 mmol, 0.14 mL), a solvent was removed with an evaporator. The remaining compound was purified by silica gel column chromatography ($CH_2Cl_2$/MeOH=6/1) to obtain a desired compound as a 1:1 diastereo mixture in a yield of 70% (59 mg).

The obtained sample (10 mg) was further purified by reverse phase HPLC (linear gradient from eluent A:eluent B=70:30 to 0:100 in 30 min, eluent A:100 mM triethylamine acetate, eluent B: 99% MeCN+1% $H_2O$).

$^1$H NMR (400 MHz, $CDCl_3$, dr=1:1) δ7.82 (2H, t, J=8.0 Hz), 7.49-7.55 (2H, m), 7.35-7.44 (2H, m), 7.22 (1H, d, J=7.6 Hz), 7.14 (1H, d, J=7.6 Hz), 6.91-7.04 (6H, m), 6.75-6.79 (2H, m), 6.54-6.56 (2H, m), 5.67 (2H, br), 5.56 (2H, br), 4.19-4.90 (8H, m), 3.95 (4H, br), 3.38-3.58 (10H, m), 2.95 (12H, s), 0.61 (3H, s), 0.58 (3H, s), 0.54 (3H, s), 0.49 (3H, s); $^{13}$C NMR (100 MHz, $CDCl_3$) δ170.9, 170.7, 156.2, 154.8, 154.4, 149.7, 139.5, 139.0, 138.8, 136.6, 136.2, 134.4, 130.5, 130.3, 130.2, 129.2, 129.1, 127.9, 126.1, 125.9, 125.7, 124.6, 124.3, 117.1, 116.7, 116.5, 116.4, 113.9, 113.7, 101.7, 91.7, 91.5, 79.7 (d, $J_{C-F}$=160 Hz), 77.4, 74.6, 74.4, 73.3, 71.0, 69.0, 61.5, 40.4, 14.3, 1.6, 1.5, 0.9, 0.6; HRMS (ESI) exact mass calcd. for $C_{31}H_{34}FNO_8Si$: m/z 596.21105 ([M+H]$^+$), found: m/z 596.21193 (+0.9 mmu).

(2) Synthesis of 2-$CH_2$F-SPiDER-RED-βGal

According to the following scheme, 2-$CH_2$F-SPiDER-RED-βGal which was an intracellularly-retainable red fluorescent probe of the present invention was synthesized.

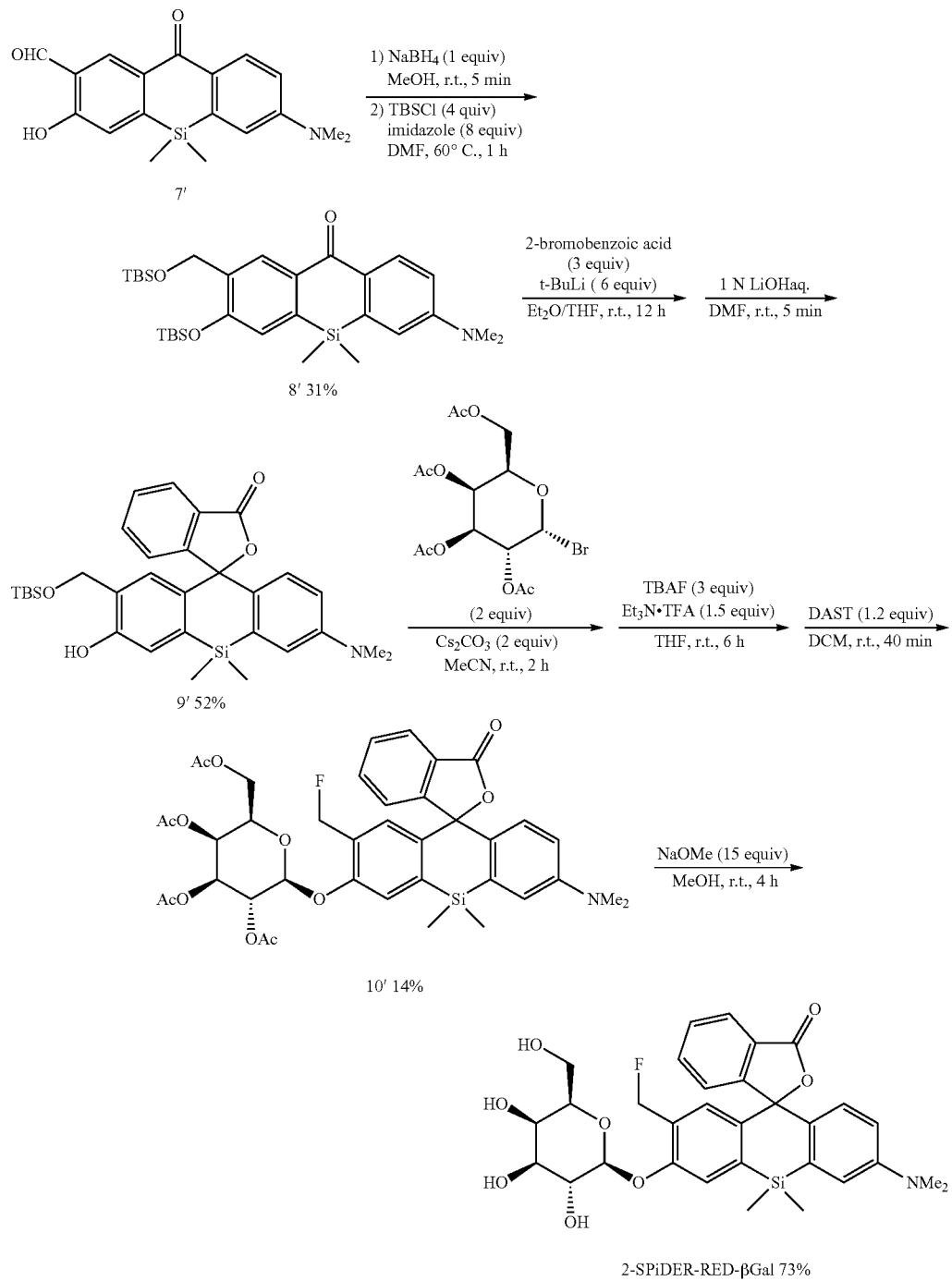
[Synthesis of Compound 7']
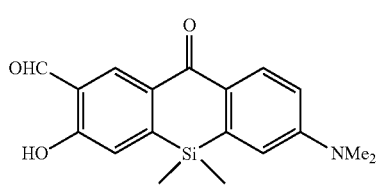 [SMILES: CN(C)c1ccc2c(c1)[Si](C)(C)c1cc(O)c(C=O)cc1C2=O]
A compound 7' was obtained as an isomer in a yield of 18% in the reaction of synthesizing the compound 7.
$^1$H-NMR (400 MHz, CDCl$_3$) δ 11.20 (1H, s), 10.04 (1H, s), 8.77 (1H, s), 8.40 (1H, d, J=9.2 Hz), 7.22 (1H, s), 6.86 (1H, dd, J=9.2 Hz, 2.8 Hz), 6.77 (1H, d, J=2.8 Hz), 3.13 (6H, s), 0.50 (6H, s); $^{13}$C-NMR (100 MHz, CDCl$_3$) δ197.7, 184.4, 162.5, 152.3, 150.5, 140.4, 136.5, 134.1, 132.6, 128.6, 121.9, 121.8, 114.5, 113.7, 40.3, −1.2; HRMS (ESI) exact mass calcd. for C$_{18}$H$_{19}$NO$_3$Si: m/z 326.12070 ([M+H]$^+$), found: m/z 326.12119 (+0.5 mmu).

[Synthesis of Compound 8']

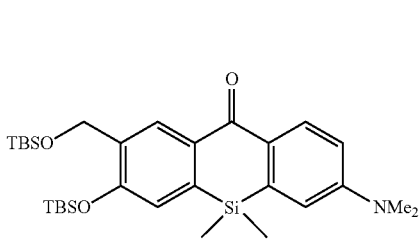 [SMILES: CN(C)c1ccc2c(c1)[Si](C)(C)c1cc(O[Si](C)(C)C(C)(C)C)c(CO[Si](C)(C)C(C)(C)C)cc1C2=O]

A compound 8' was synthesized from the compound 7' (0.06 mmol, 19 mg) according to the same procedure as that of the compound 8. By purification using PLC (hexane/Et$_2$O=5/1), a desired compound was obtained in a yield of 31% (10 mg).

$^1$H-NMR (400 MHz, CDCl$_3$) δ 8.61 (1H, s), 8.40 (1H, d, J=9.2 Hz), 6.93 (1H, s), 6.84 (1H, dd, J=9.2 Hz, 2.8 Hz), 6.78 (1H, d, J=2.8 Hz), 4.79 (2H, s), 3.10 (6H, s), 1.03 (9H, s), 0.98 (9H, s), 0.44 (6H, s), 0.28 (6H, s), 0.14 (6H, s); $^{13}$C-NMR (100 MHz, CDCl$_3$) δ185.8, 155.5, 151.9, 140.8, 139.0, 135.3, 134.5, 132.3, 130.1, 129.7, 121.7, 114.5, 113.6, 60.9, 40.4, 26.4, 26.1, 18.9, 18.7, −0.9, −3.7, −4.9; HRMS (ESI) exact mass calcd. for C$_{30}$H$_{49}$NO$_3$Si$_3$: m/z 556.30930 ([M+H]$^+$), found: m/z 556.30896 (−0.3 mmu).

[Synthesis of Compound 9']

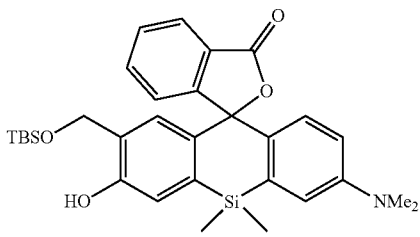 [SMILES: CN(C)c1ccc2c(c1)[Si](C)(C)c1cc(O)c(CO[Si](C)(C)C(C)(C)C)cc1C21OC(=O)c2ccccc21]

A compound 9' was synthesized from the compound 8' (0.12 mmol, 67 mg) according to the same procedure as that of the compound 9. By purification using silica gel column chromatography (hexane/CH$_2$Cl$_2$=½, 2% AcOEt), the compound 9' was obtained in a yield of 52% (34 mg).

$^1$H NMR (400 MHz, CDCl$_3$) δ8.17 (1H, s), 7.96 (1H, d, J=7.6 Hz), 7.61 (1H, t, J=7.6 Hz), 7.52 (1H, t, J=7.6 Hz), 7.23 (1H, d, J=7.6 Hz), 7.16 (1H, s), 6.94 (1H, d, J=2.8 Hz), 6.84 (1H, d, J=9.2 Hz), 6.56-6.59 (2H, m), 4.75 (1H, d, J=13 Hz), 4.69 (1H, d, J=13 Hz), 2.96 (6H, s), 0.88 (9H, s), 0.63 (3H, s), 0.58 (3H, s), 0.07 (6H, s); $^{13}$C NMR (100 MHz, CDCl$_3$) δ170.8, 155.7, 154.9, 149.2, 136.5, 135.9, 135.6, 133.9, 131.3, 128.6, 127.9, 125.9, 125.7, 125.2, 125.1, 124.0, 121.4, 116.4, 113.5, 90.8, 65.8, 40.1, 25.6, 17.9, 0.0, −1.2, −5.7; HRMS (ESI) exact mass calcd. for C$_{31}$H$_{39}$NO$_4$Si$_2$: m/z 546.24904 ([M+H]$^+$), found: m/z 546.25041 (+1.4 mmu).

[Synthesis of Compound 10']

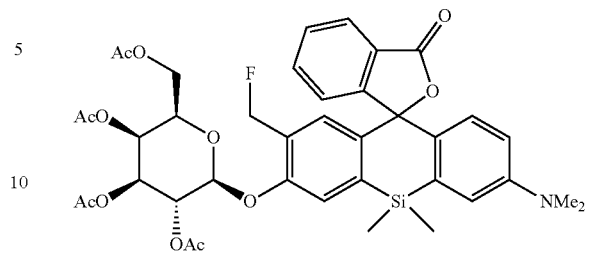

A compound 10' was synthesized from the compound 9' (0.7 mmol, 382 mg) according to the same procedure as that of the compound 10. By purification using silica gel column chromatography (hexane/AcOEt=1/1), a 1:1 diastereomeric mixture was obtained in a yield of 14% (76 mg).

$^1$H NMR (400 MHz, CDCl$_3$, dr=1:1) δ 7.99 (2H, d, J=7.2 Hz), 7.66-7.72 (2H, m), 7.60 (2H, app. t, J=7.2 Hz), 7.31-7.37 (4H, m), 6.94-6.99 (4H, m), 6.84 (1H, d, J=9.2 Hz), 6.81 (1H, d, J=8.8 Hz), 6.54-6.58 (2H, m), 4.96-5.56 (12H, m), 4.11-4.26 (6H, m), 2.97 (12H, s), 2.20 (3H, s), 2.19 (3H, s), 2.11 (3H, s), 2.10 (3H, s), 2.04 (3H, s), 2.03 (3H, s), 2.01 (6H, s), 0.67 (3H, s), 0.66 (3H, s), 0.65 (3H, s), 0.64 (3H, s); HRMS (ESI) exact mass calcd. for C$_{39}$H$_{42}$FNO$_{12}$Si: m/z 764.25331 ([M+H]$^+$), found: m/z 764.25049 (−2.8 mmu).

[Synthesis of 2-CH$_2$F-SPiDER-RED-βGal]

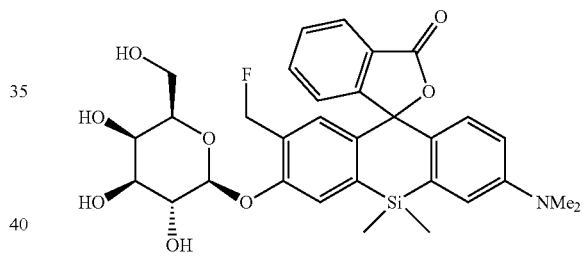

2-CH$_2$F-SPiDER-RED-βGal was synthesized from the compound 10' (0.1 mmol, 76 mg) according to the same procedure as that of 4-CH$_2$F-SPiDER-RED-βGal. By purification using silica gel column chromatography (CH$_2$Cl$_2$/MeOH=6/1), a 1:1 diastereomeric mixture was obtained in a yield of 73% (43 mg).

$^1$H NMR (400 MHz, CDCl$_3$, dr=1:1) δ 7.92 (1H, d, J=7.6 Hz), 7.83 (1H, d, J=7.6 Hz), 7.57 (2H, app. t, J=7.6 Hz), 7.44-7.50 (2H, m), 7.37 (1H, s), 7.36 (1H, s), 7.24 (1H, d, J=8.0 Hz), 7.21 (1H, d, J=7.6 Hz), 6.92 (2H, app. s), 6.88 (1H, s), 6.84 (1H, s), 6.81 (1H, d, J=9.2 Hz), 6.75 (1H, d, J=9.2 Hz), 6.50-6.57 (2H, m), 5.04-5.30 (4H, m), 4.85 (1H, d, J=7.6 Hz), 4.78 (1H, d, J=7.6 Hz), 4.28 (4H, br), 3.89-3.96 (6H, m), 3.48-3.78 (10H, m), 2.95 (6H, s), 2.94 (6H, s), 0.54 (6H, s), 0.53 (3H, s), 0.48 (3H, s); $^{13}$C NMR (100 MHz, CDCl$_3$) δ170.8, 170.6, 154.7, 154.1, 153.3, 149.6, 149.5, 140.4, 139.9, 139.4, 136.5, 135.9, 134.4, 134.2, 131.1, 131.0, 129.3, 129.2, 128.3, 126.9, 126.8 (d, J$_{C-F}$=16 Hz), 126.6 (d, J$_{C-F}$=16 Hz), 126.5, 126.2, 126.1, 124.8, 124.4, 120.7, 120.4, 116.8, 116.7, 113.7, 113.4, 101.9, 101.7, 91.2, 90.9, 80.7 (d, J$_{C-F}$=163 Hz), 77.4, 74.9, 74.6, 73.5, 71.1, 69.1, 61.8, 40.3, 0.4, 0.0, −1.2, −1.9; HRMS (ESI) exact mass calcd. for C$_{31}$H$_{34}$FNO$_8$Si: m/z 596.21105 ([M+H]$^+$), found: m/z 596.21002 (−1.0 mmu).

(3) Synthesis of 4-CH₂OH-SPiDER-RED

4-CH₂OH-SPiDER-RED which was an enzyme reaction product (or an enzyme hydrolysis product) having no monovalent group cleaved by an enzyme was synthesized by the following reaction.

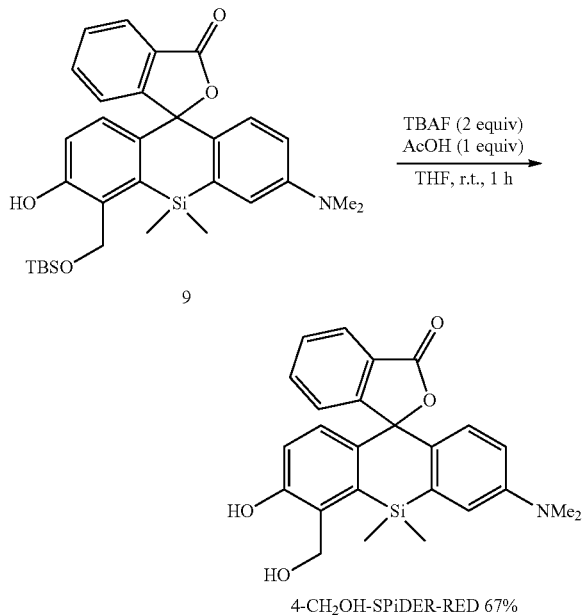 [SMILES: CN(C)c1ccc2c(c1)[Si](C)(C)c1c(ccc(O)c1CO[Si](C)(C)C(C)(C)C)C21OC(=O)c2ccccc21 ; CN(C)c1ccc2c(c1)[Si](C)(C)c1c(ccc(O)c1CO)C21OC(=O)c2ccccc21]

4-CH₂OH-SPiDER-RED 67%

TBAF (1.0 M in THF, 0.045 mmol, 45 µL) was added to a solution of the compound 9 (0.015 mmol, 8 mg), AcOH (0.015 mmol, 0.9 µL) in THF (0.5 mL) at room temperature. After the mixture was stirred for 1 hour, a solvent was removed with an evaporator, and by purification using PLC (hexane/AcOEt=5/6), a desired product was obtained in a yield of 67% (6.5 mg).

$^1$H NMR (400 MHz, CDCl$_3$) δ 7.94 (1H, d, J=7.6 Hz), 7.60 (1H, t, J=7.6 Hz), 7.50 (1H, t, J=7.6 Hz), 7.21 (1H, d, J=7.6 Hz), 6.92-6.94 (2H, m), 6.83 (1H, d, J=8.8 Hz), 6.78 (1H, d, J=8.8 Hz), 6.60 (1H, dd, J=8.8 Hz, 2.8 Hz), 5.11 (2H, s), 2.96 (6H, s), 0.73 (3H, s), 0.67 (3H, s); $^{13}$C NMR (100 MHz, CDCl$_3$) δ171.2, 156.6, 155.6, 149.8, 137.2, 135.8, 135.1, 134.4, 130.4, 129.2, 129.1, 128.2, 126.2, 126.1, 124.3, 118.8, 116.5, 114.3, 91.9, 64.4, 40.6, 1.7, 1.6; HRMS (ESI) exact mass calcd. for C$_{25}$H$_{25}$NO$_4$Si: m/z 432.16256 ([M+H]$^+$), found: m/z 432.16280 (+0.2 mmu).

(4) Synthesis of 2-CH₂OH-SPiDER-RED

According to the following reaction, 2-CH₂OH-SPiDER-RED which was a comparative compound having no monovalent group cleaved by an enzyme was synthesized.

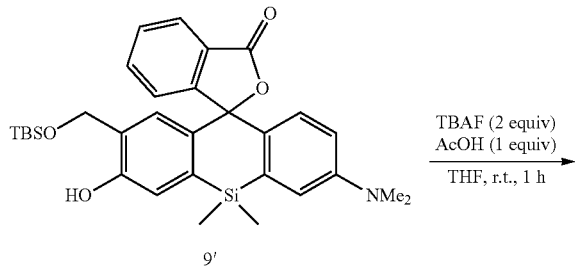

-continued

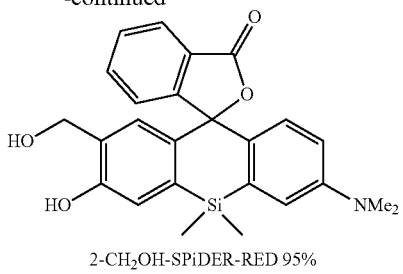

2-CH₂OH-SPiDER-RED 95%

2-CH₂OH-SPiDER-RED was synthesized from the compound 9' (0.02 mmol, 10 mg) by the same procedure as that of 4-CH₂OH-SPiDER-RED. By purification using PLC (hexane/AcOEt=5/6), a desired product was obtained in a yield of 95% (8.4 mg).

$^1$H NMR (400 MHz, CDCl$_3$) δ7.96 (1H, d, J=7.6 Hz), 7.61 (1H, t, J=7.6 Hz), 7.53 (1H, t, J=7.6 Hz), 7.23 (1H, d, J=7.6 Hz), 7.19 (1H, s), 6.94 (1H, d, J=2.8 Hz), 6.83 (1H, d, J=8.8 Hz), 6.62 (1H, s), 6.57 (1H, dd, J=8.8 Hz, 2.8 Hz), 4.71 (1H, d, J=13 Hz), 4.66 (1H, d, J=13 Hz), 2.96 (6H, s), 0.63 (3H, s), 0.58 (3H, s); $^{13}$C NMR (100 MHz, CDCl$_3$) δ170.8, 155.6, 154.8, 149.3, 137.6, 136.1, 135.8, 134.0, 131.2, 128.8, 128.0, 126.3, 126.0, 125.8, 125.5, 124.1, 121.4, 116.4, 113.5, 90.9, 64.8, 40.2, 0.0, −0.1; HRMS (ESI) exact mass calcd. for C$_{25}$H$_{25}$NO$_4$Si: m/z 432.16256 ([M+H]$^+$), found: m/z 432.16085 (−0.2 mmu).

Example 2

Changes in Absorption and Fluorescence Spectra by Enzyme Reaction

For the probe compounds of the present invention obtained in Example 1 (4-CH₂F-SPiDER-RED-βGal and 2-CH₂F-SPiDER-RED-βGal), changes in absorption and fluorescence spectra according to the addition of β-galactosidase were measured. The measurement results of 4-CH₂F-SPiDER-RED-βGal are shown in FIG. 1, and the measurement results of 2-CH₂F-SPiDER-RED-βGal are shown in FIG. 2.

FIG. 1(a) shows the fluorescence intensity of 4-CH₂F-SPiDER-RED-βGal by an enzyme reaction upon lapse of time. Measurements were carried out by adding 5U (3-galactosidase to 4-CH₂F-SPiDER-RED-βGal prepared at 1 µM in a PBS buffer solution. The measurement conditions are as follows: an excitation wavelength of 610 nm, a fluorescence wavelength of 638 nm, a measurement time of 3600 seconds, a slit (excitation/fluorescence) of 2.5 nm/2.5 nm, and a photomultiplier voltage of 700 V. FIG. 1(b) shows an absorption spectrum of a 1 µM 4-CH₂F-SPiDER-RED-βGal PBS buffer solution before adding 5U β-galactosidase and for 1 hour after the addition. FIG. 1(c) shows a fluorescence spectrum of a 1 µM 4-CH₂F-SPiDER-RED-βGal PBS buffer solution before adding 5U β-galactosidase and for 1 hour after the addition. The measurement conditions are as follows: an excitation wavelength of 610 nm, a slit (excitation/fluorescence) of 2.5 nm/2.5 nm, and a photomultiplier voltage of 700 V.

FIG. 2(a) shows the fluorescence intensity of 2-CH₂F-SPiDER-RED-βGal by an enzyme reaction upon lapse of time. Measurements were carried out by adding 5U β-galactosidase to 2-CH₂F-SPiDER-RED-βGal prepared at 1 µM in a PBS buffer solution. The measurement conditions are as follows: an excitation wavelength of 610 nm, a fluorescence wavelength of 638 nm, a measurement time of 3600 seconds, a slit (excitation/fluorescence) of 2.5 nm/2.5 nm, and a photomultiplier voltage of 700 V. FIG. 2(b) shows an absorption spectrum of a 1 μM 2-CH$_2$F-SPiDER-RED-βGal PBS buffer solution before adding 5U β-galactosidase and for 1 hour after the addition. FIG. 2(c) shows a fluorescence spectrum of a 1 μM 2-CH$_2$F-SPiDER-RED-βGal PBS buffer solution before adding 5U β-galactosidase and for 1 hour after the addition. The measurement conditions are as follows: an excitation wavelength of 610 nm, a slit (excitation/fluorescence) of 2.5 nm/2.5 nm, and a photomultiplier voltage of 700.

These results showed that 2-CHF$_2$-SPiDER-RED-βGal and 4-CHF$_2$-SPiDER-RED-βGal emit fluorescence specifically in response to enzyme activity of β-galactosidase. It was found that 4-CHF$_2$-SPiDER-RED-βGal shows higher reactivity with β-galactosidase and a higher fluorescence increasing rate than 2-CHF$_2$-SPiDER-RED-βGal.

Example 3

Labeling of Fluorescent Dye to BSA Protein by β-Galactosidase Enzyme Reaction in Presence of BSA Protein Using 4-CH$_2$F-SPiDER-RED-βGal and 2-CH$_2$F-SPiDER-RED-βGal which are the probe compounds of the present invention obtained in Example 1, we have demonstrated that these compounds cleaved by β-galactosidase fluorescently label bovine serum albumin (BSA) protein coexisting therewith in a solution. The measurement results of 4-CH$_2$F-SPiDER-RED-βGal are shown in FIG. 3, and the measurement results of 2-CH$_2$F-SPiDER-RED-βGal are shown in FIG. 4.

Using 1) 10 μL of a PBS buffer solution containing 10 μM 4-CH$_2$F-SPiDER-RED-1Gal, 1 mg/mL BSA, and 5U β-galactosidase, 2) 10 μL of a PBS buffer solution containing 10 μM 4-CH$_2$F-SPiDER-RED-βGal and 1 mg/mL BSA, 3) 10 μL of a PBS buffer solution containing 10 μM 4-CH$_2$F-SPiDER-RED-βGal and 5U β-galactosidase, 4) 10 μL of a PBS buffer solution containing only 10 μM 4-CH$_2$F-SPiDER-RED-βGal, and 5) 10 μL of a PBS buffer solution containing 10 μM 4-CH$_2$OH-SPiDER-RED, the reaction products were subjected to SDS-PAGE (running gel: 10%, stacking gel: 4%, electrophoresis voltage: 200 V). Each gel obtained by SDS-PAGE was illuminated with excitation light having a wavelength of 488 nm, and fluorescence in the 540 to 600 nm range was observed at a PMT voltage of 1000 V (FIG. 3(a)). After observation, each gel was Coomassie stained and the position of the BSA on the gel was confirmed (FIG. 3(b)).

FIGS. 4(a) and 4(b) show the results of similar measurement using 10 μM 2-CH$_2$F-SPiDER-RED-βGal instead of 10 μM 4-CH$_2$F-SPiDER-RED-βGal.

By the reaction of the probe compound of the present invention with β-galactosidase in the presence of BSA, fluorescence response was observed at the position of BSA after SDS electrophoresis. On the other hand, fluorescence was not observed for the sample containing no β-galactosidase or the sample using 4-CH$_2$OH-SPiDER-RED as Comparative Example.

These results suggest that the probe compound of the present invention changes in response specifically to β-galactosidase activity, and thereby being covalently bonded to BSA. The above results demonstrate that a protein coexisting in a solution can be fluorescently labeled in enzyme-activity-specific fashion through use of the enzyme-specific retainable fluorescent compound of the present invention. Even when 2-CHF$_2$-SPiDER-RED-βGal was used, BSA was fluorescently labeled, but its reactivity with the enzyme was low, whereby fluorescence intensity was lower than that of 4-CHF$_2$-SPiDER-RED-βGal.

Example 4

Fluorescence Imaging of Living Cells Expressing β-Galactosidase

We have examined whether the probe compound of the present invention can be used for fluorescence imaging of a living cell.

4-CHF$_2$-SPiDER-RED-βGal was added to a dish in which cells expressing β-galactosidase (HEK-lacZ) and cells not expressing β-galactosidase (HEK) were co-cultured, and incubated at 37° C. for 30 minutes. The HEK cells were previously stained with CellTracker (TM) Green. A fluorescence image and a transmitted light image were acquired using a confocal microscope (TCS SP5X; manufactured by Leica). White light laser (WLL) was used as laser, and HCX PL APO CS 40×/1.25 (40 times, manufactured by Leica) was used as an objective lens. The observation conditions were as follows: an excitation wavelength: 594 nm, a fluorescence wavelength: 610 to 700 nm, and a scale: 25 μm. The obtained living cell fluorescence imaging is shown in FIG. 5.

Cells were observed without being washed with culture medium after incubation with the test compound 4-CHF$_2$-SPiDER-RED-βGal, and as a result, red fluorescence derived from the test compound was observed only in HEK-lacZ cells. On the other hand, in the HEK cells not expressing β-galactosidase, no red fluorescence signal was obtained (left side of FIG. 5).

These results demonstrate that the fluorescent probe of the present invention is effective for fluorescent detection of living cell β-galactosidase activity at a single-cell level.

Example 5

Non-Fixed Fluorescence Imaging of Living Biological Tissue Having β-Galactosidase Activity Next, we have examined whether the probe compound of the present invention, 4-CHF$_2$-SPiDER-RED-βGal, can be applied to fluorescence imaging of living biological tissues by using *drosophila* tissues.

(Materials and Methods)

Wing discs of a *drosophila* (*Drosophila melanogaster*, en-lacZ/dpp-GFP) expressing β-galactosidase and GFP in some tissues were incubated with 4-CHF$_2$-SPiDER-RED-βGal and Hoechst 33342 at room temperature for 2 hours, and then observed under a confocal microscope (TCS SP8, manufactured by Leica). White light laser (WLL) was used as laser, and HCX PL APO CS 40×/1.25 (40 times, manufactured by Leica) was used as an objective lens. The measurement conditions are as follows: excitation wavelengths: 405 nm (Hoechst 33342), 488 nm (GFP), 594 nm (4-CHF$_2$-SPiDER-RED-βGal), fluorescence wavelengths: 420 to 490 nm (Hoechst 33342), 490 to 570 nm (GFP), 601 to 681 nm (4-CHF$_2$-SPiDER-RED-βGal), and a scale: 75 μm. The obtained live tissue fluorescence imaging is shown in FIG. 6.

(Results)

It was shown that selective fluorescence imaging of the region having β-galactosidase activity was possible by using 4-CHF$_2$-SPiDER-RED-βGal because the fluorescent dye (which was the enzyme reaction product) shows no diffusion of fluorescence.

These results demonstrate that through use of the intracellularly-retainable red fluorescent probe such as 4-CHF$_2$-

SPiDER-RED-βGal of the present invention, the cell expressing β-galactosidase in the living biological tissue can be detected at a single-cell level, and simultaneous observation with GFP and Hoechst is possible.

The invention claimed is:

1. An intracellularly-retainable red fluorescent probe comprising a compound represented by the following formula (I) or a salt thereof:

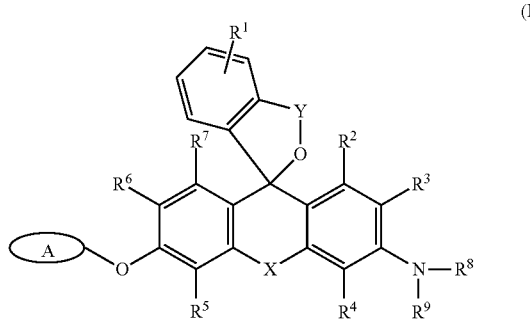

wherein:
A represents a monovalent group cleaved by an enzyme;
$R^1$ represents a hydrogen atom, or one to four of the same or different substituents bonded to a benzene ring;
$R^3$ and $R^6$ each independently represent —$CFR^{10}R^{11}$, —$CF_2R^{12}$, a hydrogen atom, a hydroxyl group, an alkyl group, or a halogen atom,
$R^4$ and $R^5$ each independently represent —$CFR^{10}R^{11}$, —$CF_2R^{12}$, a hydrogen atom, a hydroxyl group, or an alkyl group,
wherein at least one of $R^3$, $R^4$, $R^5$, and $R^6$ is —$CFR^{10}R^{11}$ or —$CF_2R^{12}$;
$R^2$ and $R^7$ each independently represent a hydrogen atom, a hydroxyl group, an alkyl group, or a halogen atom;
$R^8$ and $R^9$ each independently represent a hydrogen atom or an alkyl group;
$R^{10}$, $R^{11}$, and $R^{12}$ each independently represent a hydrogen atom, an alkyl group, or an alkenyl group;
X represents Si($R^a$)($R^b$), wherein $R^a$ and $R^b$ each independently represent a hydrogen atom or an alkyl group; and
Y is —C(=O)— or —$R^c$C(=O)—, wherein $R^c$ is an alkylene group having 1-3 carbon atoms.

2. The intracellularly-retainable red fluorescent probe according to claim 1, wherein the enzyme is a hydrolase containing a reporter enzyme.

3. The intracellularly-retainable red fluorescent probe according to claim 2, wherein the reporter enzyme is β-galactosidase, β-lactamase, alkali phosphatase, luciferase, or peroxidase.

4. The intracellularly-retainable red fluorescent probe according to claim 1, wherein the enzyme is an enzyme expressed or activated specifically in a cancer cell.

5. The intracellularly-retainable red fluorescent probe according to claim 1, wherein A is a galactopyranosyl group.

6. The intracellularly-retainable red fluorescent probe according to any one of claims 1 to 5, wherein at least one of $R^3$, $R^4$, $R^5$, and $R^6$ is —$CFR^{10}R^{11}$.

7. The intracellularly-retainable red fluorescent probe according to any one of claims 1 to 5, wherein at least one of $R^3$, $R^4$, $R^5$, and $R^6$ is —$CH_2F$.

8. An intracellularly-retainable red fluorescent probe comprising a compound represented by the following formula (Ia) or (Ib) or a salt thereof:

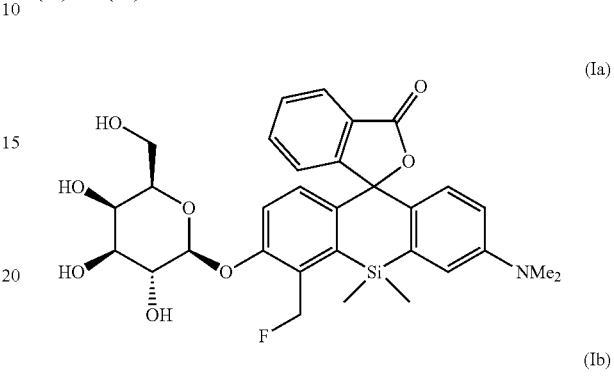

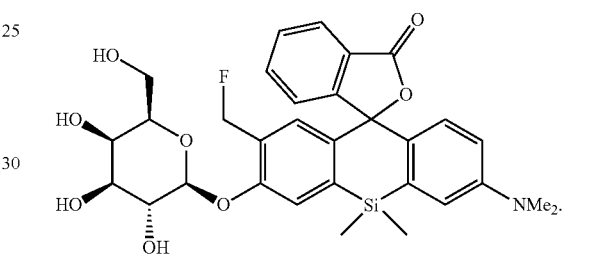

9. A kit for detecting or visualizing a target cell expressing a specific enzyme,
the kit comprising the intracellularly-retainable red fluorescent probe according to claim 1.

10. The composition or kit according to claim 9, wherein the target cell is a cell expressing β-galactosidase.

11. The composition or kit according to claim 9, wherein the target cell is a cancer cell.

12. A method for detecting a target cell expressing a specific enzyme by using the intracellularly-retainable red fluorescent probe according to claim 1.

13. The method according to claim 12, comprising the steps of:
bringing the intracellularly-retainable red fluorescent probe into contact with an enzyme expressed specifically in the target cell at ex vivo; and
inducing fluorescence by excitation light irradiation.

14. The method according to claim 12, wherein the target cell is a cell expressing β-galactosidase.

15. The method according to claim 12, wherein the target cell is a cancer cell.

* * * * *